(12) United States Patent
Schlam et al.

(10) Patent No.: US 12,239,178 B2
(45) Date of Patent: Mar. 4, 2025

(54) DERMAL HEATSINK EXHIBITING HYDROPHILIC AND CONTAMINANT RESISTANT PROPERTIES AND METHOD FOR FABRICATING A DERMAL HEATSINK

(71) Applicant: Omius Inc., Palo Alto, CA (US)

(72) Inventors: Gustavo Cadena Schlam, Monterrey (MX); Michel Romero Flores, Monterrey (MX)

(73) Assignee: Omius Inc., Palo Alto, CA (US)

( * ) Notice: Subject to any disclaimer, the term of this patent is extended or adjusted under 35 U.S.C. 154(b) by 0 days.

(21) Appl. No.: 18/124,283

(22) Filed: Mar. 21, 2023

(65) Prior Publication Data

US 2023/0329383 A1    Oct. 19, 2023

Related U.S. Application Data

(63) Continuation of application No. 17/037,457, filed on Sep. 29, 2020, now Pat. No. 11,632,996, which is a
(Continued)

(51) Int. Cl.
*A61F 7/00* (2006.01)
*A41D 13/005* (2006.01)
(Continued)

(52) U.S. Cl.
CPC .......... *A42B 1/008* (2013.01); *A41D 13/0053* (2013.01); *A41D 13/0056* (2013.01); *A41D 20/005* (2013.01); *A61F 7/00* (2013.01); *B05D 3/002* (2013.01); *B05D 3/007* (2013.01); *B05D 3/0453* (2013.01); *B05D 3/107* (2013.01);
(Continued)

(58) Field of Classification Search
None
See application file for complete search history.

(56) References Cited

U.S. PATENT DOCUMENTS 10,820,652 B2 * 11/2020 Schlam ................ B05D 3/0453
2009/0317709 A1 * 12/2009 Brazis .................. H01M 4/663
252/502

(Continued)

FOREIGN PATENT DOCUMENTS

JP          2011031541 A    *  2/2011

*Primary Examiner* — Jeffrey A Vonch
(74) *Attorney, Agent, or Firm* — Run8 Patent Group, LLC; Peter Miller; Leah Raddatz

(57) ABSTRACT

One variation of a method for fabricating a dermal heatsink includes: fabricating a substrate defining an interior surface, an exterior surface opposite the interior surface, and an open network of pores extending between the interior surface and the exterior surface; activating surfaces of the substrate and walls of the open network of pores; applying a coating over the substrate to form a heatsink, the coating comprising a porous, hydrophilic material and defining a void network; removing an excess of the coating from the substrate to clear blockages within the open network of pores by the coating; hydrating the heatsink during a curing period; heating the heatsink during the curing period to increase porosity of the coating applied over surfaces of the substrate; and rinsing the heatsink with an acid to decarbonate the coating along walls of the open network of pores in the substrate.

18 Claims, 7 Drawing Sheets

Related U.S. Application Data continuation of application No. 16/574,048, filed on Sep. 17, 2019, now Pat. No. 10,820,652.

(60) Provisional application No. 62/732,193, filed on Sep. 17, 2018.

(51) Int. Cl.

| | | |
|---|---|---|
| *A41D 20/00* | (2006.01) | |
| *A42B 1/008* | (2021.01) | |
| *B05D 3/00* | (2006.01) | |
| *B05D 3/04* | (2006.01) | |
| *B05D 3/10* | (2006.01) | |
| *B23P 15/26* | (2006.01) | |
| *B32B 5/18* | (2006.01) | |
| *F28F 13/00* | (2006.01) | |
| *F28F 13/18* | (2006.01) | |
| *A41D 1/04* | (2006.01) | |
| *B05D 3/02* | (2006.01) | |
| *C04B 28/00* | (2006.01) | |
| *C04B 28/18* | (2006.01) | |
| *F28D 21/00* | (2006.01) | |

(52) U.S. Cl.
CPC .............. *B05D 3/108* (2013.01); *B23P 15/26* (2013.01); *F28F 13/003* (2013.01); *F28F 13/185* (2013.01); *A41D 1/04* (2013.01); *A41D 13/0058* (2013.01); *A41D 2300/20* (2013.01); *A61F 2007/0001* (2013.01); *A61F 2007/0007* (2013.01); *A61F 2007/0018* (2013.01); *A61F 2007/0034* (2013.01); *A61F 2007/0098* (2013.01); *B05D 3/0254* (2013.01); *B05D 2203/30* (2013.01); *C04B 28/005* (2013.01); *C04B 28/182* (2013.01); *F28D 2021/0029* (2013.01); *F28F 2245/02* (2013.01); *F28F 2260/00* (2013.01); *Y10T 428/12479* (2015.01); *Y10T 428/24008* (2015.01); *Y10T 428/24017* (2015.01); *Y10T 428/24174* (2015.01); *Y10T 428/24331* (2015.01); *Y10T 428/24339* (2015.01); *Y10T 428/2457* (2015.01); *Y10T 428/24612* (2015.01); *Y10T 428/249967* (2015.04); *Y10T 428/249968* (2015.04); *Y10T 428/249981* (2015.04)

(56) References Cited

U.S. PATENT DOCUMENTS

2011/0020631 A1\* 1/2011 Miller ................. C04B 38/0022
428/319.3
2016/0235535 A1\* 8/2016 Wooley ................. A61L 27/422

\* cited by examiner

DERMAL HEATSINK EXHIBITING HYDROPHILIC AND CONTAMINANT RESISTANT PROPERTIES AND METHOD FOR FABRICATING A DERMAL HEATSINK

CROSS-REFERENCE TO RELATED APPLICATIONS

This application is a continuation of U.S. patent application Ser. No. 17/037,457, filed on 29 Sep. 2020, which is a continuation of U.S. patent application Ser. No. 16/574,048, filed on 17 Sep. 2019, which claims the benefit of U.S. Provisional Application No. 62/732,193, filed on 17 Sep. 2018, each of which is incorporated in its entirety by this reference.

TECHNICAL FIELD

This invention relates generally to the field of heat transfer and more specifically to a new and useful dermal heatsink and a method for fabricating the dermal heatsink in the field of heat transfer.

DESCRIPTION OF THE EMBODIMENTS

Figure 1A:
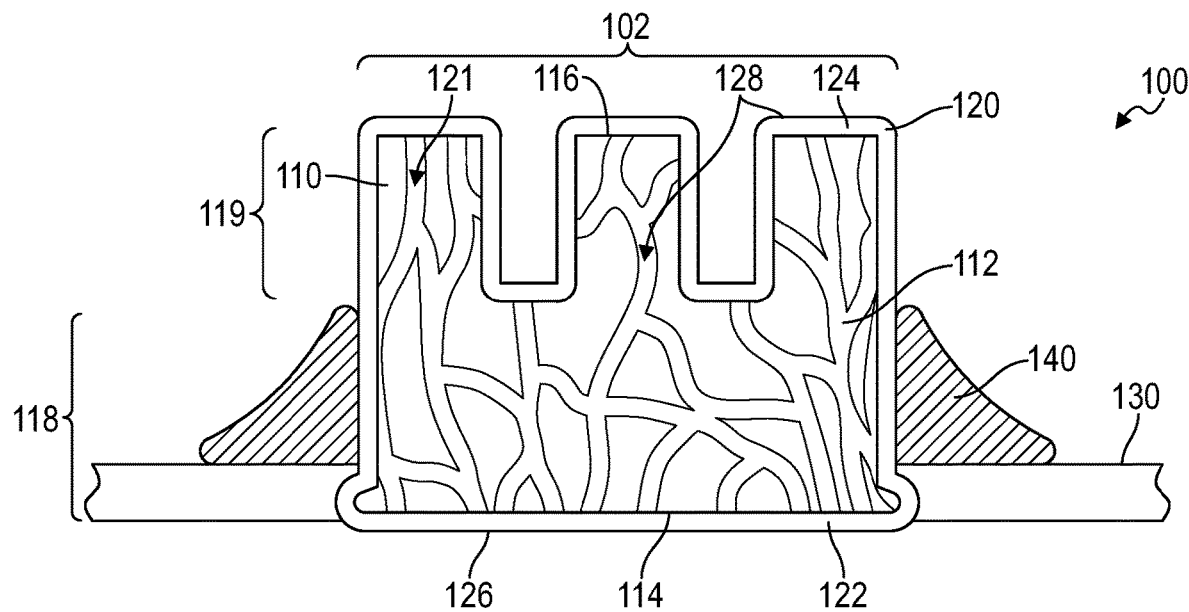
FIGS. 1A and 1B are schematic representations of a dermal heatsink.

The following description of embodiments of the invention is not intended to limit the invention to these embodiments but rather to enable a person skilled in the art to make and use this invention. Variations, configurations, implementations, example implementations, and examples described herein are optional and are not exclusive to the variations, configurations, implementations, example implementations, and examples they describe. The invention described herein can include any and all permutations of these variations, configurations, implementations, example implementations, and examples.

1. Apparatus

As shown in FIGS. 1A, 1B, 2A and 2B, a dermal heatsink 100 includes a heatsink 102 including a substrate 110 that defines: an interior surface 114 configured to thermally couple to a heat source 150; an exterior surface 116; and an open network of pores 112 extending between the interior surface 114 and the exterior surface 116. The heatsink 102 also includes a coating 120: defining a porous, hydrophilic material; defining a void network 121 configured to filter hydrophobic molecules; extending across the interior surface 114 of the substrate 110; and lining the open network of pores 112 within the substrate 110. The substrate no and the coating 120 of the heatsink 102 cooperate to wick moisture from a surface of the heat source 150, through the void network 121 lining the open network of pores 112, to the exterior surface 116.

2. Method

Figure 4A:
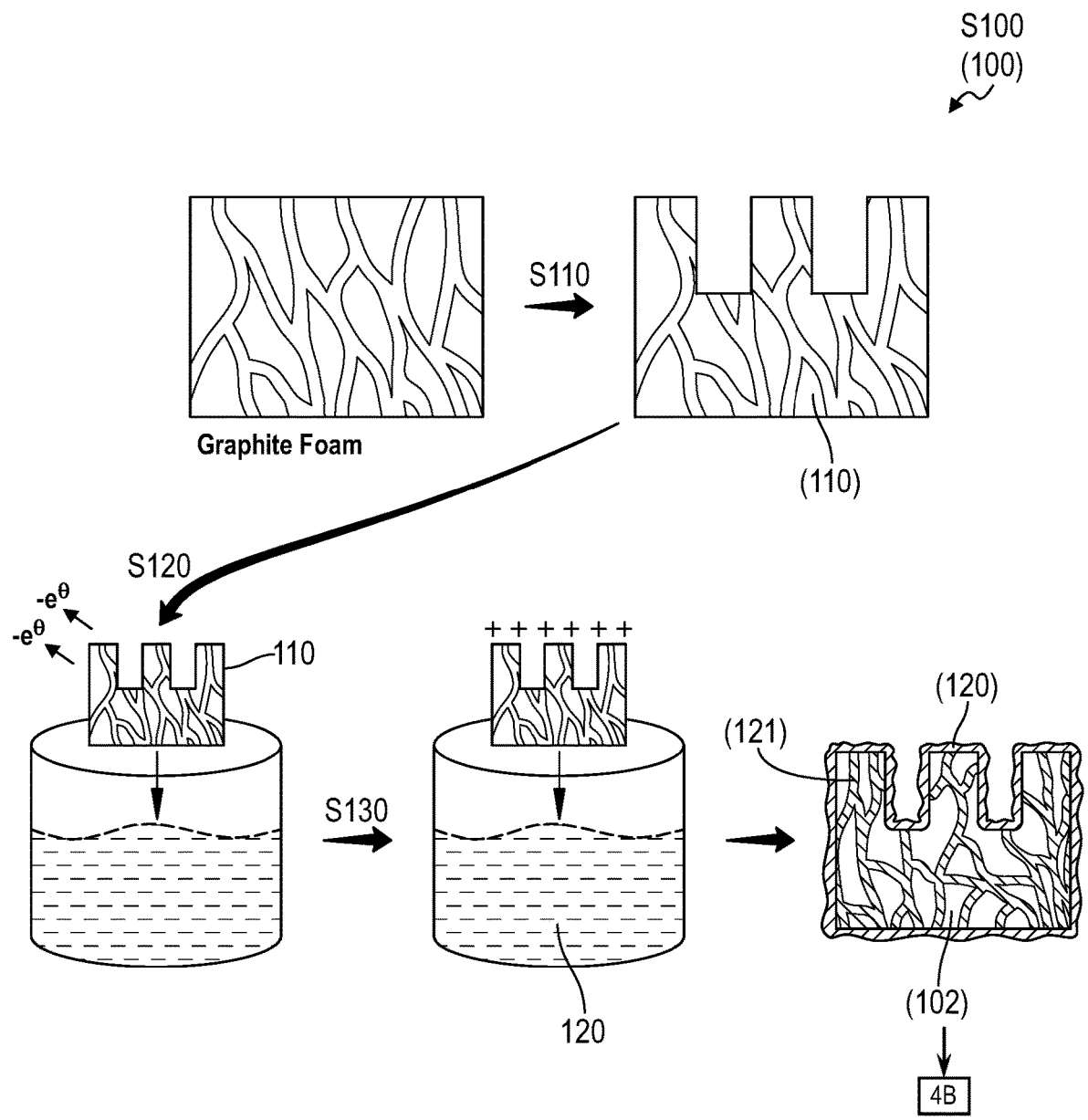
FIGS. 4A, 4B, and 4C are a flowchart representation of a method.
Figure 4B:
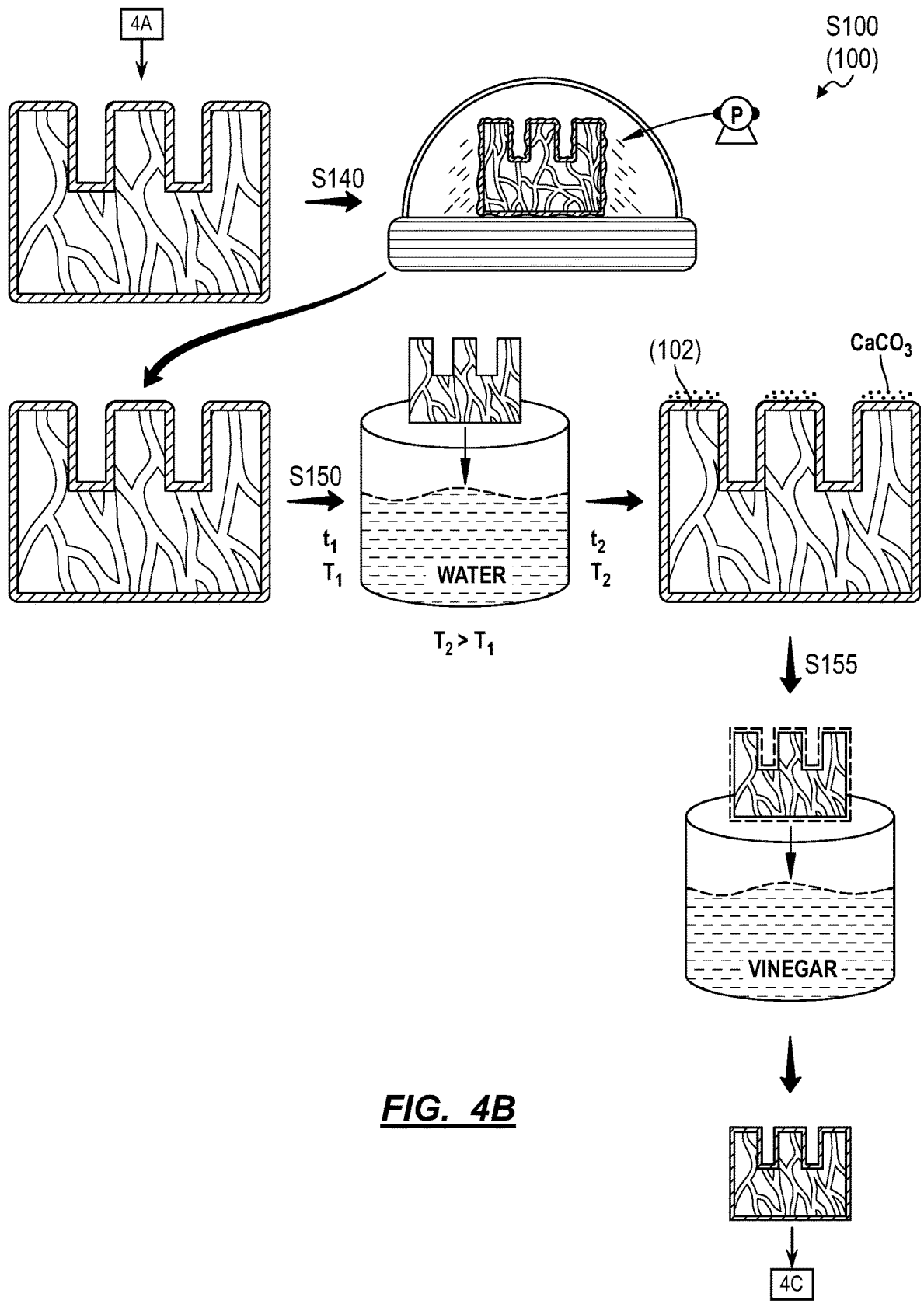

As shown in FIGS. 4A and 4B, a method S100 for fabricating a hydrophilic, contaminant resistant dermal heatsink 100 includes: fabricating a substrate 110 defining an interior surface 114, an exterior surface 116, and an open network of pores 112 extending between the interior surface and the exterior surface in Block S110; activating surfaces of the substrate 110 and walls of the open network of pores 112 in Block S120; applying a coating 120 over the substrate 110 to form a heatsink 102 in Block S130, the coating 120 comprising a porous hydrophilic material; removing an excess of the coating 120 from the substrate 110 to clear blockages within the open network of pores 112 by the coating 120 in Block S140; hydrating the heatsink 102 during a curing period in Block S150; heating the heatsink 102 during the curing period in Block S150 to increase porosity of the coating 120 applied over surfaces of the substrate 110; and rinsing the heatsink 102 with an acid to decarbonate the coating 120 along walls of the open network of pores 112 in the substrate 110 in Block S155.

Figure 4C:
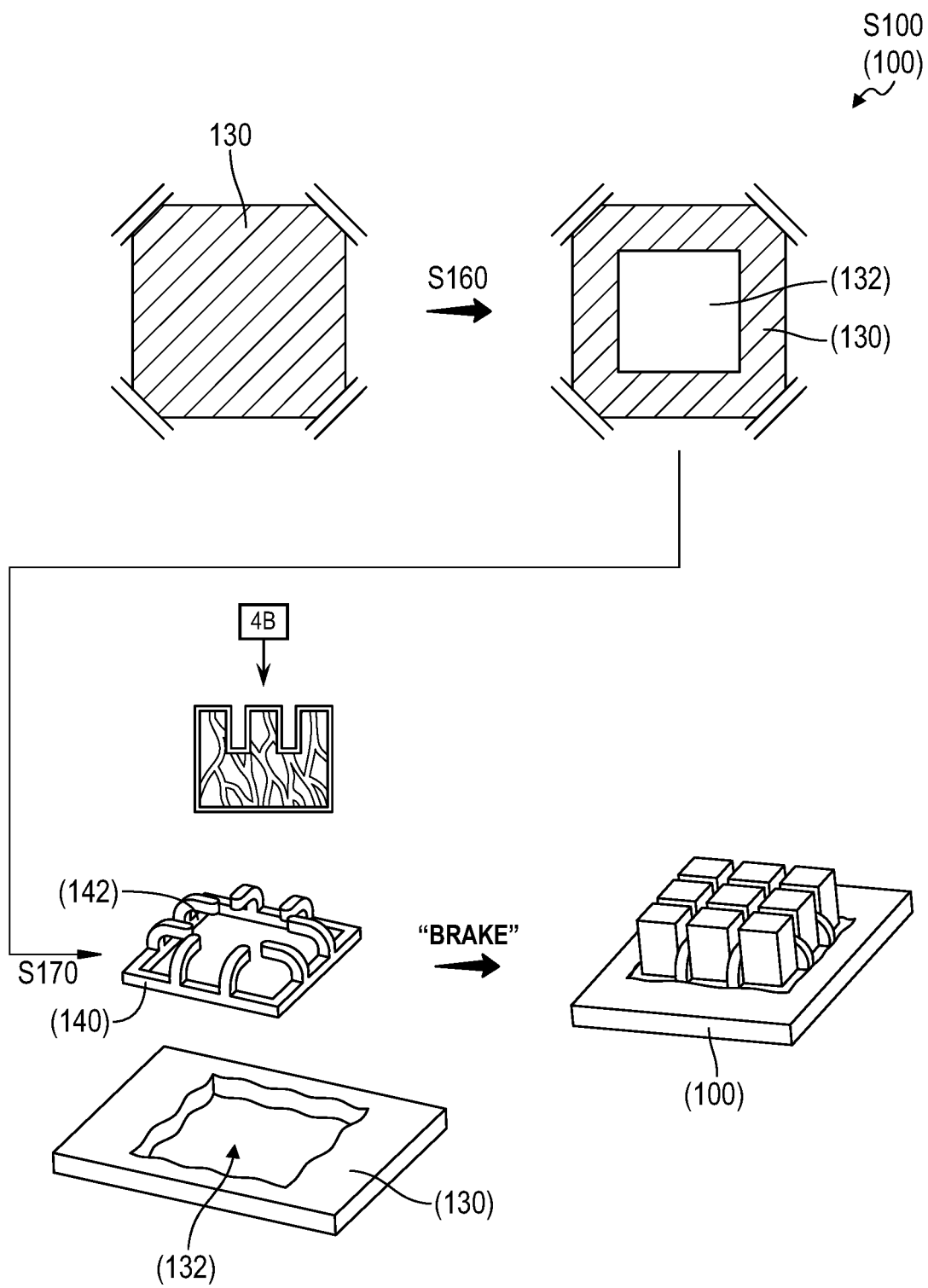

As shown in FIG. 4C one variation of the method S100 further includes: forming a first aperture 132 in a textile panel 130 in Block S160; locating the heatsink 102 within the first aperture 132 in the textile panel 130; locating a heatsink retainer 140 about a periphery of the first aperture 132 in the textile panel 130, the heatsink retainer 140 defining a set of claws 142 extending over channels defined by the heatsink 102; and bonding the heatsink retainer 140 to the textile panel 130 about a periphery of the first aperture 132 in Block S170, the set of claws 142 securing the heatsink 102 within the first aperture 132.

3. Applications

The method S100 can be executed to fabricate a heatsink 102 that includes: a substrate 110 defining an open network of pores 112 (or "open-celled pores" or "channels"); and a coating 120 of a porous hydrophilic material that lines internal and external surfaces of the substrate 110—including walls of the open network of pores 112 in the substrate. The coating 120 can form a robust shell around the substrate and can function to wick moisture from a contact surface 126 at one side of the heatsink 102 in contact with a human user's skin, transport this moisture through the open network of pores 112 in the substrate (e.g., via capillary action), and raise this moisture to an evaporative surface 128 defined by surfaces of the coating 120 at an opposite side of the heatsink 102 and within the internal network of pores 112. The evaporative surface 128 can span a set of fins across the heatsink 102 and may be cooled via evaporative cooling as moisture—drawn from the contact surface 126 through the void network 121 of the coating 120 lining the open network of pores in the substrate 110—evaporates. Accordingly, the substrate 110 draws heat from the user's skin at the contact surface 126 and conducts this heat to the evaporative surface 128, which releases this heat to the environment (e.g., via convection and radiation), thereby cooling the user. In particular, the method S100 can be executed to fabricate a heatsink 102 that includes a conductive, porous substrate 110 lined with a hydrophilic, porous coating 120 such that the heatsink 102: defines a dense open network of pores 112 with sufficient pore size such that air may flow freely through pores and the available surface area for application of the coating 120 is increased. The coating 120 defines a void network 121 (or "porous microstructure") with minimal void (or "pore") size exhibiting low resistance to transport of moisture (e.g., high permeability to water) between the contact surface 126 (adjacent the interior surface 114 of the substrate no) and surfaces of the coating 120 within the open network of pores 112 and the evaporative surface 128

(adjacent the external surface of the substrate 110), and exhibits high resistance to transport of other organic molecules (e.g., oils) through the void network 121. For example, the dense open network of pores 112 defined by the heatsink 102 can exhibit pore sizes large enough to be lined by the coating 120 and for effective flow of air through pores in the open network of pores 112, and the coating 120 can be processed such that at room temperature conditions, the void network 121 of the coating 120 is hydrated (e.g., the pores are filled with water molecules) and therefore hydrophilic (e.g., attracted to water molecules) and contaminant resistant due to the size of pores in this void network 121 (e.g., larger hydrophobic molecules cannot displace the smaller water molecules present in these hydrated pores). The heatsink 102 may therefore be hydrophilic and exhibit contaminant resistant properties (e.g., contaminant resistant) properties due to the hydrated void network 121 of the coating 120 lining the open network of pores 112.

The resulting heatsink 102 can thus define: a porous, thermally-conductive structure (i.e., the substrate no) with a network of interconnected pores encased in a rigid, hydrophilic shell (i.e., the coating 120) that exhibits greater affinity to polar substances (e.g., water) than to non-polar substance (e.g., oil). The coating 120 thus forms hydrophilic surfaces that are resistant to hydrophobic contaminants, such as volatile organic compounds (VOCs) and oils; by spanning interior and exterior surfaces of the substrate 110, the coating 120 thus increases hydrophilicity and increases resistance of the heatsink 102. More specifically, this greater affinity of the coating 120 to polar substances enables water to wet surfaces of the heatsink 102 when oils and other contaminants are present at these surfaces, such as at the contact surface 126 when the contact surface 126 is placed in contact with a user's forehead, forearm, or chest. Additionally, because the coating 120 exhibits a relatively high affinity to polar substances, the heatsink 120 may be quickly cleaned of oils and other contaminants by rinsing with water and/or surfactants (e.g., soap). Therefore, a heatsink 102 defining a durable, contaminant resistant wicking structure (e.g., heatsink) exhibiting hydrophilicity, contaminant resistance, and high thermal conductivity can be fabricated according to Blocks of the method S100.

In one variation, the heatsink 102 can be incorporated into a textile or wearable article of clothing to form a wearable dermal heatsink 100. For example, the heatsink 102 can be mounted or adhered over a bore (or an "open") defined in a forehead area of a headband, in a chest area of a shirt, in a torso area of a vest, or in a forearm area of an armband or wristband. In particular, the heatsink 102 can be mounted or coupled to the textile such that the contact surface 126 of the heatsink 102 contacts skin of the user when the dermal heatsink 100 is worn by a user. Furthermore, multiple instances of the heatsink 102 can be incorporated into the dermal heatsink 100 in order to achieve contact between contact surfaces 126 of units of the heatsink 102 while enabling the dermal heatsink 100 to conform to the user's (unique) body (e.g., forehead, abdomen) geometry during use.

A user may therefore wear the dermal heatsink 100— including one or multiple instances of the heatsink 102 arranged over corresponding bores in the dermal heatsink 100—to wick moisture (i.e., sweat) from regions of her skin in contact with these heatsinks 102 and to cool (e.g., via evaporative cooling) these regions of her body. In particular, a heatsink 102 integrated into the dermal heatsink 100 a) defines an evaporative surface 128 that defines a larger surface area than the area of the user's skin in contact with the contact surface 126 of the heatsink 102 and b) absorbs heat from the user via the contact surface 126, thereby increasing an effective surface area of the user's skin. By absorbing moisture (e.g., sweat) from the user's skin and transporting this moisture from the contact surface 126 to the evaporative surface 128—defined by coating-air interfaces including surfaces of an interior shell of the coating 120 lining the open network of pores 112 and of an exterior shell of the coating 120 lining the exterior surface of the substrate—the heatsink increases a rate of evaporative cooling across the larger surface area of the evaporative surface 128 and internal coating 120 surfaces, thereby increasing a rate of heat transfer out of the adjacent region of the user's skin and increasing a rate of cooling of the user's body. Furthermore, because the heatsink 102 exhibits contaminant resistance, the heatsink may exhibit low propensity to absorb oil from the user's skin, thereby limiting uptake of oils from the user's skin, limiting fouling by natural oils produced by the user, maintaining high permeability of water (e.g., sweat) from the user's skin, and maintaining a high rate of evaporative cooling even during extended periods of use by the user.

A user may wear the dermal heatsink 100 on regions of the skin corresponding a high density of blood vessels to increase total body cooling, and/or on regions of the skin where a body may produce heat at a higher rate (e.g., a human forehead). For example, a set of heatsinks 102 can be incorporated into a textile panel 130 to define a dermal heatsink 100 in the form of a headband. A user may wear this headband while running a marathon (e.g., over two hours) or cycling a century ride (e.g., over seven hours) to extract heat from the user's head and cool the user more generally at a rate: proportional to the user's sweat rate; proportional to the user's speed (which affects a rate of airflow over the heatsink 102); and therefore approximately proportional to the user's power output during exercise.

In another example, a set of heatsinks 102 are incorporated into a textile panel 130 to define a dermal heatsink 100 in the form of a vest. In this example, rather than immerse a hyperthermic patient in an ice bath or spray a mist at the hyperthermic patient, medical staff may douse the vest with water, place the vest on a hyperthermic patient, and place the patient near a fan in order to consistently extract heat at a high rate from the patient's torso. In particular, when paired with a fan, the wetted vest may achieve a high rate of cooling for the hyperthermic patient in a wide variety of environments: with minimal setup time (e.g., compared to an ice bath or mist system); without risking tissue damage from prolonged contact with chilled fluid; without necessitating consumption of a large volume of water; without substantively increasing local humidity (e.g., compared to a mist); without producing a spill hazard from a liquid spill; and at a rate more isolated from ambient wind and temperature conditions than a mist system.

4. Terms

As described above, the coating 120 defines a hydrophilic cementitious mixture lining surfaces of the substrate 110 and walls of the network of pores 112 such that the formed heatsink exhibits hydrophilic behavior enabling the flow of moisture (e.g., water) through the void network 121 of the coating 120 lining the open network of pores 112 within the heatsink 102, the interior surface 114 and the exterior surface 116. Additionally, the coating 120 functions as a hydrophilic layer over the substrate 110, such that water may flow freely through the substrate 110 from the contact surface 126 of the coating 120 to the evaporative surface 128 of the coating 120 and displace oils and/or other hydrophobic contaminants clogging the open network of pores 112.

The coating 120 exhibits a greater affinity to polar substances (e.g., water) than to nonpolar substances (e.g., oil). This higher affinity to polar substances enables moisture to wet the coating 120 and therefore surfaces of the heatsink 102. Additionally, because the coating 120 exhibits a higher affinity to water than oils and other contaminants, in the presence of both, the coating 120 can interact with water molecules rather than the oil molecules, thus exhibiting contaminant resistant tendencies. Furthermore, when oils are present on surfaces of the heatsink 102, water in sweat or from an external source can more readily displace these oils from surfaces of the heatsink 102.

The substrate 110 defines an open network of pores 112 extending between an interior surface 114 of the substrate no and an exterior surface 116 of the substrate 110. The network of pores 112 includes open-cell pores that can extend from the interior surface 114 to the exterior surface 116. The substrate no can define this network of pores 112 at substantially uniform density throughout its volume. The sizes of pores in the open network of pores 112 are sufficiently large such that air and moisture may flow through the open network of pores 112. At these sizes, oils and other contaminants may enter and/or clog the open network of pores. Therefore, the coating 120 interacts with surfaces of the open network of pores 112 to form a hydrophilic layer lining these surfaces, such that water may flow through the open network of pores 112 and displace contaminants. Therefore, the heatsink 102 is contaminant resistant in that the interactions between the network of pores 112 within the substrate no and the void network 121 of the coating 120 increases hydrophilic tendencies (e.g., increases an affinity for water molecules) and reduces hydrophobic interactions (e.g., lowers an affinity for hydrophobic molecules).

5. Example

Figure 2A:
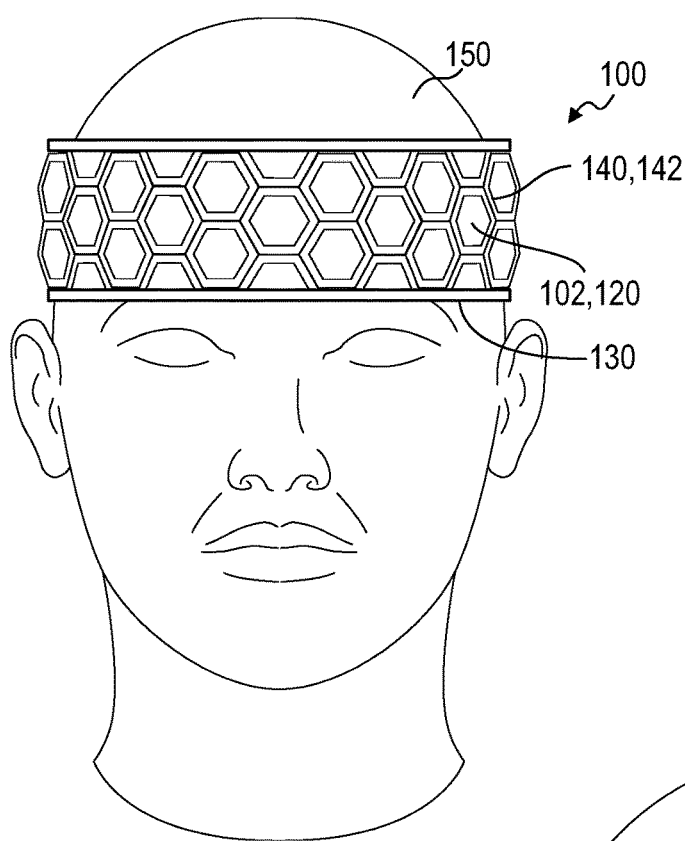
FIGS. 2A and 2B are schematic representations of the dermal heatsink.
Figure 2B:
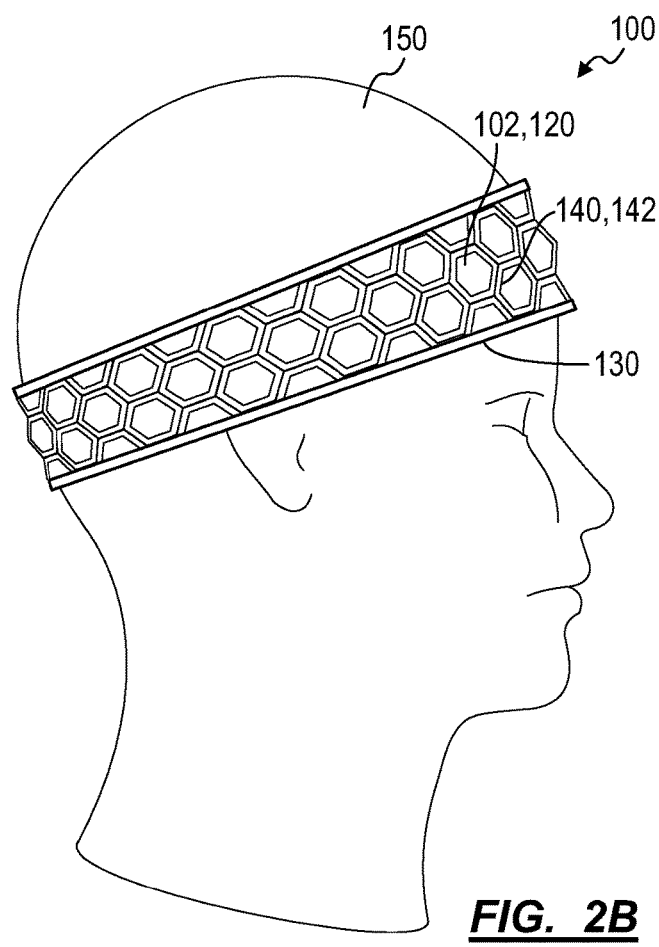
Figure 3A:
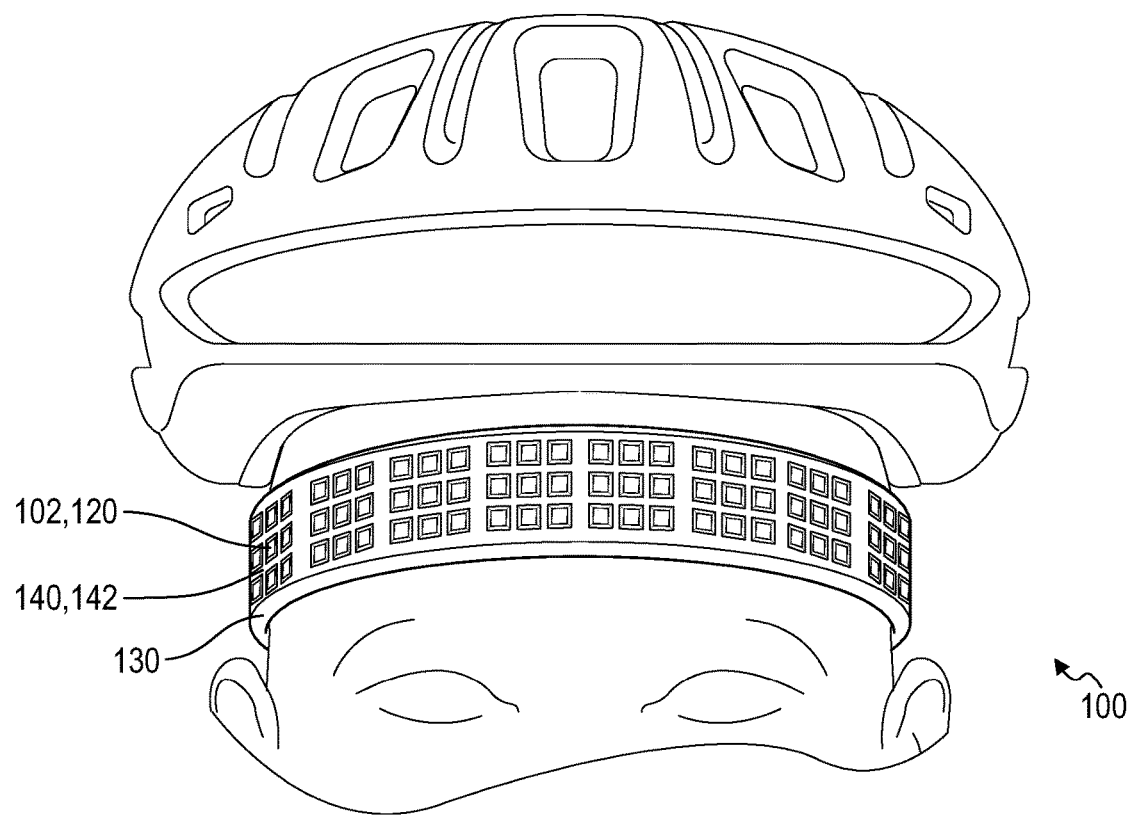
FIGS. 3A, 3B, 3C, and 3D are schematic representations of variations of the dermal heatsink.

In one implementation, the dermal heatsink 100 is a headband 160 configured to be worn by a user about her forehead as shown in FIGS. 2A, 2B, and 3A. The headband 160 can be worn during exercise by the user to wick sweat from the forehead of the user and to cool the user as a body temperature of the user increases during exercise. As shown in FIGS. 2A, 2B, and 3A, the headband 160 includes: a set of heatsinks 102, each heatsink in the set of heatsinks 102 configured to wick moisture from the forehead of the user and to cool a temperature of the user; and a textile panel 130 in which the set of heatsinks 102 are arranged, such that when the textile panel 130 is attached to the forehead of the user, the set of heatsinks 102 contact skin of the user.

Each heatsink can define: a substrate 110 machined from a thermally-conductive graphite foam and defining an open network of pores extending between surfaces of the substrate no; and a hydrophilic, contaminant resistant coating defining a cementitious mixture and extending across surfaces of the substrate no and lining the open network of pores 112 within the substrate 110. Therefore, the heatsink 102 exhibits high thermal conductivity and is sufficiently hydrophilic such that the heatsink 102 can dissipate heat from the body of the user and wick moisture (e.g., water in sweat of the user) through the open network of pores 112. Each heatsink can include a set of fins 119 configured to increase heat dissipation by increasing surface area of the heatsink 102. For example, the substrate 110 can further define: a base 118 defining an interior surface 114 of the substrate 110; and a set of fins 119 extending from the base 118 opposite the interior surface 114 and defining an exterior surface 116 of the substrate 110.

In this implementation, each heatsink is attached to a textile panel 130 configured to be worn on the forehead of the user. For example, the headband 160 can include a textile panel 130 defining an aperture in which a heatsink 102 is arranged. The heatsink 102 is arranged in the aperture and attached to the textile panel 130 via a heatsink retainer 140 encircling the conductive substrate. The heatsink retainer 140 can be a square shaped, thermoplastic polymer and is configured to improve the mechanical properties and attachment of the conductive heatsink to the textile. The heatsink retainer 140 can adhere to the textile panel 130 via partially melting or injecting the frame into the textile panel 130 and the thermally conductive heatsink. In one variation, a first heatsink retainer 140 is attached to the textile panel 130 about a periphery of an aperture defined by the textile panel 130. After the first heatsink retainer 140 is attached to the textile panel 130, the heatsink 102 can be arranged in the aperture. Then, a second heatsink retainer 140 can be melted or injected into the textile panel 130 and the heatsink 102 to secure the heatsink 102 within the aperture of the textile panel 130. Additionally, the heatsink retainer 140 can define a set of claws 142 that further secure the heatsink 102 within the aperture of the textile panel 130 and secure attachment of the heatsink 102 to the retainer 140 during the melting or injection process. For example, the heatsink retainer 140 can define a set of claws that extend between fins of the heatsink 102 to further secure the heatsink 102 on the textile panel 130.

The headband 160 can be manufactured to include a set of apertures (e.g., via laser cutting or mechanical cutting), each aperture in the set of apertures configured to fit a heatsink 102. For example, the textile panel 130 can include a set of ten heatsinks 102 arranged into two symmetrical rows of heatsinks 102. The textile panel 130 including the heatsinks 102 can be incorporated (e.g., via sewing techniques) into a wearable headband 160. When a user wears the headband 160 across her forehead, gaps between heatsinks 102 on the textile panel 130 enable the textile panel 130 to conform to a curvature or shape of her forehead. In one variation, as shown in FIG. 2, the heatsinks 102 are arranged in a Voronoi pattern on the textile panel 130, such that the heatsinks 102 vary in size and shape to account for the natural shape of a human forehead. Alternatively, the headband 160 can include heatsinks 102 with a particular shape and size and arranged in a particular geometry according to the curvature and forehead shape of a particular user.

As shown in FIG. 3A, a user may wear the headband 160 across her forehead when exercising to wick sweat from her body and cool her body temperature. The user may wear the headband 160 with the interior surface 114 of the substrate 110 in contact with skin (e.g., on the forehead) of the user. The hydrophilic, contaminant resistant coating of the heatsink 102 enables moisture (e.g., sweat) on the forehead of the user to be absorbed by the interior surface 114 of the substrate 110, pass through the network of pores within the substrate 110, and exit to the evaporative surface 128 of the coating 120, lining the exterior surface 116 of the substrate no interior surfaces of the coating 120 within the network of pores 112, where the moisture evaporates.

The heatsink 102 dissipates heat from the user via evaporation of moisture present at the surface of the coating 120. Therefore, when a user initially wears the dermal heatsink 100, a rate of heat transfer may be low as little to no moisture has been absorbed by the heatsink 102. To increase the initial rate of heat transfer, a user may moisten or drench the dermal heatsink 100 with liquid before and/or during physical activity to activate the heatsink 102 such that heat transfer from the user to the heatsink 102 begins immediately when the user begins a physical activity and continues throughout performance of the physical activity. A user may drench the apparatus with water from an external source such as a hose. Alternatively, in one variation, the apparatus can include a wearable tank that can administer liquid to the heatsinks 102.

As maximum heat transfer occurs when air flows through the apparatus (e.g., via increased evaporation and heat exchange via convection), the dermal heatsink 100 can operate at different rates of cooling based on air flow rates and angles of the airflow at which airflow contacts the heatsinks 102. Therefore, a user may experience different rates of cooling depending on weather, physical activity, and motion of the user. For example, a first user biking outdoors with natural airflow may experience a greater cooling effect than a second user exercising on a stationary bike indoors. To increase the cooling effect, the second user exercising indoors on the stationary bike may locate a fan in front of the stationary bike to simulate natural airflow and thus achieve a similar cooling effect as the first user biking outdoors. In one variation, to increase airflow through the heatsink 102, the heatsink 102 can exhibit a geometry such that vortices are formed on the exterior surface 114 of the heatsink 102, thereby increasing airflow and reducing drag.

6. Substrate

Generally, the heatsink 102 includes a substrate 110 defining: an interior surface 114 configured to thermally couple to a heat source 150; an exterior surface 116; and an open network of pores extending between the interior surface 114 and the exterior surface 116. More specifically, the substrate no exhibits a particular geometry including a fin side defining the exterior surface 116, and a body side defining the interior surface 114. The substrate no is lined with a porous, hydrophilic coating to form the heatsink 102. The substrate no further defines: a base 118 defining the interior surface 114, the base 118 exhibiting a first surface area; and a set of fins 119 extending from the base 118 opposite the interior surface 114, the set of fins 119 exhibiting a second surface area greater than the first surface area and defining the exterior surface 116.

The substrate 110 exhibits a high thermal conductivity and is configured to dissipate heat from a heat source 150 (e.g., transfer heat from a heat source 150 to the exterior surface 116 of the substrate 110). The interior surface 114 of the substrate no is configured to thermally couple to the heat source 150 to enable heat dissipation from the smaller surface area of the interior surface 114 to the greater surface area of the evaporative surface 128, defined by the surface area of the exterior surface 116 (e.g., the fins of the substrate no) and the surface area of the walls of the network of pores 112. A coating deposited over surfaces of the substrate 110 to increase hydrophilicity of the heatsink 102 may exhibit decreased thermal conductivity of the heatsink 102. Therefore, a material exhibiting high thermal conductivity can be machined or molded to form the substrate no in order to maximize the thermal conductivity of the heatsink 102 after addition of the coating 120 to surfaces of the substrate 110.

The thermally conductive substrate can exhibit a porous structure and define an open network of pores, through which moisture can flow from the interior surface 114 of the substrate no to the exterior surface 116 of the substrate 110. These pores exhibit sufficiently small volumes such that moisture can be absorbed through the pores via capillary action, while larger molecules contained in oils and other contaminants cannot travel through the pores.

For example, the substrate no can define an open network of pores including pores exhibiting pore diameters between 275-microns and 325-microns such that sufficient capillary pressure is generated for water to flow through the open network of pores 112. In a similar example, the substrate 110 defines the open network of pores 112 exhibiting a pore size less than 400 microns, and the coating 120 defines a thickness between 50 microns and 200 microns to yield an effective pore size less than 100 microns on walls of the open network of pores 112 in the substrate no. The substrate no and the coating 120—in the completed heatsink 102— can therefore cooperate to wick moisture (e.g., sweat) from the interior surface to the exterior surface via the open network of pores 112 (e.g., via capillary action) when the heatsink 102 is in contact with a user's skin.

Additionally, the substrate 110 may exhibit higher mechanical durability with decreased pore size. Therefore, the substrate no can include more intricate base and fin features which may increase a rate of heat dissipation from a heat source 150 to the heatsink 102.

The substrate can be formed from a thermally conductive foam such as: aluminum foam, copper foam, or graphite foam. These foams exhibit porous structures and therefore exhibit relatively high specific surface areas (e.g., surface area per volume). Thermally conductive foams also exhibit relatively lower density than traditional metals included in heat sinks, due to their porous structure.

In one implementation, the substrate 110 is machined from a thermally conductive graphite material defining an open network of pores. The conductive graphite material can be a graphite foam (e.g., Graphite Foam produced by C-FOAM Corporation of Western Australia). For example, the substrate 110 can be machined from a block of graphite foam, the graphite foam exhibiting high thermal conductivity and low density. Generally, graphite foams can be made by: selecting a mold configured to shape the graphite foam and applying a mold release agent to walls of the mold; introducing a quantity of pitch to the mold; purging the mold of air via applying a vacuum or introducing an inert fluid; heating the pitch in the mold to a sufficient temperature such that the pitch coalesces into a liquid (e.g., between 50° Celsius and 100° Celsius higher than the softening point of the pitch); releasing the vacuum and applying an inert fluid at a static pressure (e.g., approximately 1000-psi); further heating the pitch to a high temperature such that gases evolve and foam the pitch; and further heating the pitch to a higher temperature to coke the pitch before cooling the pitch to room temperature, while gradually releasing the applied static pressure. The resulting porous graphite foam may be machined to form the substrate 110.

In one implementation, the substrate 110 is molded from a metallic material, such as aluminum or copper. In this implementation, the substrate no can be molded to fit a particular size and geometry.

The substrate 110 can be machined to a particular shape and size. In one variation, the substrate 110 exhibits a quadrangular prism shape and defines straight, narrow channels on an upper section of the substrate no to form a set of fins 119. The substrate 110 can include the set of fins 119 to increase a surface area of the exterior surface 116, and therefore increase the rate of heat dissipation from a heat source 150. The interior surface 114 of the substrate no can be straight or curved to match a shape of regions of the human body. For example, the interior surface 114 of a substrate no may be curved to fit the curvature of a forehead of user. Alternatively, the interior surface 114 of the substrate 110 may be flat (e.g., straight edges) and include gaps between heatsinks 102 to enable bending or greater flexibility of the dermal heatsink 100 about regions of the body such that the dermal heatsink 100 can be worn by different users and conform to each user accordingly.

7. Coating

Figure 1B:
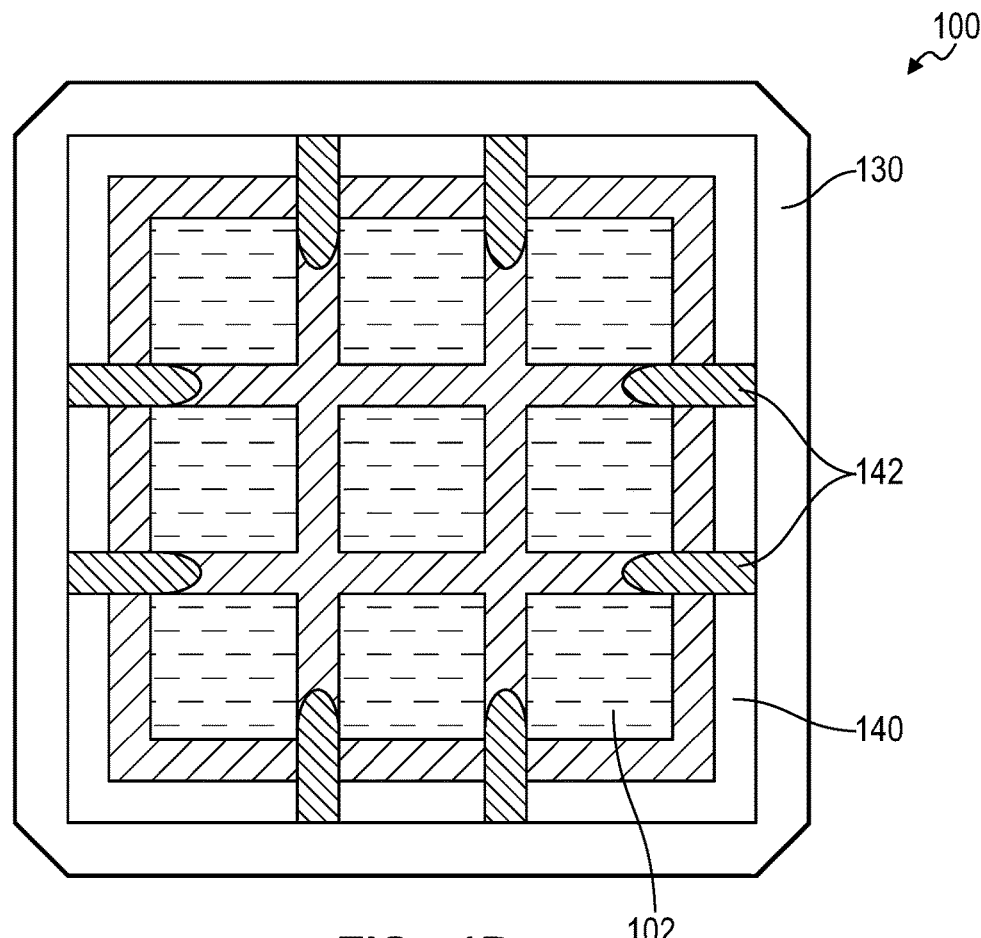

As shown in FIGS. 1A and 1B, the heatsink 102 includes a coating 120 lining each surface of the substrate 110 and the walls of pores in the networks of pores within the substrate 110. The coating 120 forms: an interior shell 122 extending across the interior surface 114 of the substrate 110 and defining a contact surface 126 configured to contact skin of a user, the contact surface 126 defining a first area; and an exterior shell 124 extending across the exterior surface 116 of the substrate 110 and defining an evaporative surface 128 of a second area greater than the first area.

Generally, the coating 120 functions as a hydrophilic shell cooperating with the substrate 110 to enable moisture wicking from skin of a user across a contact surface 126 of the coating 120, through the open network of pores 112 of the substrate 110, and across an evaporative surface 128 of the coating 120, and to provide durability to the heatsink 102 structure. The coating 120 can define a cementitious mixture exhibiting high water concentration such that the water molecules in the coating 120 attract water molecules in moisture passing through the open network of pores 112 within the substrate 110, therefore exhibiting hydrophilic properties. The coating 120 also functions as a contaminant resistant layer to prevent contaminants such as oils from clogging the open network of pores 112.

The coating 120 can define a thin shell of approximately uniform thickness that: extends across the exterior surface 116 of the substrate 110; extends across the interior surface 114 of the substrate 110; and lines the walls of the open network of pores 112 within the substrate 110. In particular, the coating 120 can be of at least a minimum thickness across the surfaces of the substrate 110 in order to increase durability of the heatsink 102 and increase resistance of the heatsink 102 to oils and other contaminants. The coating 120 can be less than a maximum thickness in order to maintain the open network of pores 112 within the substrate 110 and preserve the heat exchanger properties of the structure provided by the substrate 110, as the coating 120 is less thermally conductive than the substrate 110. For example, the heatsink 102 can include a substrate 110 machined from a graphite foam material and exhibiting a first impact resistance. The heatsink 102 can also include a coating: defining a cementitious matrix and exhibiting a second impact resistance greater than the first impact resistance, such that coating increases a durability of the heatsink 102; and exhibiting a thickness between 75-microns and 125-microns.

In one implementation, the coating 120 is a cementitious mixture of distilled water and cement (e.g., Portland white cement). To prepare the coating 120 for application onto the substrate 110, a volume of water is mixed with a volume of cement (and an aggregate) at a water-cement ratio that—when cured—yields a heterogeneous microstructure including a pore structure, cement, and interfacial transition zone that are permeable to water. More specifically, the coating 120 can harden as a result of a chemical reaction between water and cement in this cementitious mixture. At a low water-cement ratio (e.g., less than 0.4), this reaction in the coating 120 is fully hydrated but may exhibit a water permeability insufficient to wet and fully coat the substrate 110. Further, at low and moderate water-cement ratios (e.g., 0.35 to 0.65), the coating 120 may exhibit minimal porosity, exhibit a network of narrow pores, and thus exhibit relatively low permeability to water when cured. Therefore, the coating 120 can be prepared with a relatively high water-cement ratio (e.g., greater than 0.7; or within the range of 0.78 to 0.82) such that the reaction between water and cement in the cementitious mixture yields excess water as the coating 120, thereby resulting in the coating 120 exhibiting a highly porous microstructure that is permeable to water, therefore resulting in greater moisture flux through the resulting heatsink 102.

For example, the coating 120 can define a cementitious mixture of water and calcium silicate cement mixed at a water-cement ratio between 0.8 and 1.0 to achieve high porosity and increase hydrophilic tendencies of the coating 120.

Furthermore, the coating 120 defines a void network 121 configured to filter hydrophobic molecules and increase the hydrophilicity of the coating 120 and thereby the heatsink 102. The coating 120 can define the void network 121 including: micropores that wick water through the coating 120, and that exhibit a first size smaller than pores in the network of pores 112; and nanopores that are hydrated at standard conditions (e.g.,) to increase the hydrophilicity of the coating 120, and that exhibit a second size smaller than the first size such that larger hydrophobic molecules cannot displace water in the hydrated nanopores. The coating 120—defining this void network 121—lines the network of pores 112 of the substrate 110 to wick moisture through the coating 120 while larger pores in the network of pores 112 provide an increased heat exchange surface and enable airflow through the heatsink 102.

7.1 Coating Additives

As shown in FIG. 1, the coating 120 lines each surface of the substrate 110 and walls of the network of pores within the substrate 110. In one variation, the coating 120 includes an additive that reduces viscosity of the cementitious mixture such that the cementitious mixture can fully cover and wet external surfaces of the substrate 110 and walls of the internal network of pores within the substrate 110. For example, the coating 120 can include superplasticizers that increase fluidity of the cementitious mixture. Additionally or alternatively, the coating 120 can include surfactants that lower surface tension and therefore increase fluidity of the cementitious mixture.

As shown in FIG. 1, the coating 120 lines each surface of the substrate 110 and walls of the network of pores within the substrate 110 to form a hydrophilic, highly-permeable porous structure (e.g., the heatsink 102). In one variation, the coating 120 includes aggregates that increase hydrophilicity of the coating 120. For example, the coating 120 can include Silica Fume aggregates that increases the resistant hydrophilicity of the coating 120 and therefore increases a rate of moisture wicking through the resulting heatsink 102.

Additionally and/or alternatively, cement colorants may be added to the mixture of water and cement. These cement colorants can be added to the coating 120 at concentrations ranging from three percent to ten-percent of the weight of the coating 120. The addition of cement colorants to the coating 120 can enable detection of defects in the coating 120 such as chips, breaks, fractures, etc. For example, the coating 120 can include a cement colorant corresponding to particular pigment. After application of the coating 120 on the substrate 110, the coating 120 cures on surfaces of the substrate. The pigment, defined by the cement colorant, may collect or separate on these surfaces to reveal fractures in the coating 120. The addition of cement colorants to the coating 120 can also enable detection of salt and/or dirt present on surfaces of the heatsink 102. For example, the coating 120 can include a cement colorant corresponding to a red pigment. As salt collects on surfaces of the heatsink 102 from skin of a user sweating while wearing the dermal heatsink 102, the heatsink may require cleaning by the user to remove salt and/or other contaminants. In this example, the pigment of the salt is distinct from the pigment of the coating 120. Therefore, the user may easily see that the dermal heatsink is dirty (e.g., collecting salt) and requires cleaning. In another example, a high contrast of the pigment from the color of substrate may indicate to a user to dispose of or replace the dermal heatsink 100. Alternatively, no cement colorants may be added to the mixture of water and cement. For example, a white coating may be mixed from Portland white cement and water. The coating 120 may be left white in order to reflect a maximum amount of light, thereby increasing the cooling effect of the dermal heatsink 100 when worn by a user.

8. Substrate Fabrication

Block S110 of the method S100 recites fabricating the substrate. In particular, in Block S110, the substrate 110 can be fabricated to form a base 118 defining and a set of fins 119 extending from the base 118. For example, the substrate 110 can define a rectangular base with a row of rectangular fins or a grid array of square fins (shown in FIGS. 1A and 1B) extending upwardly from the rectangular base. In another example, the substrate no includes: a base defining a polygonal cross-section according to a cell in a Voronoi pattern; and a set of fins arranged in a row, grid array, or nested Voronoi pattern and extending upwardly from the base.

In one implementation, the substrate 110 is fabricated by machining a porous, thermally-conductive material. In one example, the substrate 110 is machined from a block of graphite foam. In this example, the block of graphite foam can define a material exhibiting: relatively high thermal conductivity compared to common metal conductors (e.g., copper); a low density (e.g., less than 0.6 $g/cm^3$); and relatively uniform pore size (e.g., approximately between 0.8 and 1.6 millimeters) such that air may flow through these pores. In another example, graphite powder can be printed, injection-molded, sintered, and/or cast to form the substrate 110.

In a similar example, the substrate 110 is fabricated from porous graphite defining the open network of pores 112. The open network of pores 112 exhibits pore size less than 1.5 millimeters such that when the coating 120 is later applied to the substrate no and an excess coating is removed, the open network of pores 112 exhibits an effective pore size less than 1.2 millimeters through the heatsink 102. However, the substrate no can be formed in any other way and in any other geometry.

9. Substrate Preparation

The substrate 110 can then be cleaned to remove oils and other contaminants. For example, the substrate no can be cleaned with a set of solvents by rinsing the substrate no with these solvents or by implementing an ultrasonic cleaning process for approximately fifteen minutes. Solvents in the set of solvents can include: acetone, isopropyl alcohol, ethanol, and other solvents. After cleaning the substrate no with the set of solvents, the substrate 110 can be dried. In one variation, the substrate 110 may be rinsed with distilled water to remove solvents from the surfaces and pores of the substrate 110 before the substrate no is dried.

Initially, surfaces of the substrate no and walls of the open network of pores 112 may exhibit low compatibility (e.g., may not react or bond) with the coating 120. Therefore, the surfaces of the substrate 110 can be functionalized to increase a presence of hydrophilic functional groups on these surfaces, such that the coating 120 (e.g., the cementitious mixture) may exhibit stronger bonds with the surfaces of the substrate no via hydroxide ions of the coating 120 and hydrophilic functional groups on these surfaces. The surfaces of the substrate 110 can be oxidized to increase compatibility between the substrate 110 and the coating 120. Additionally or alternatively, surfaces of the substrate 110 can be etched to increase surface roughness and therefore increase an interface area between the substrate 110 and the coating 120.

10. Substrate Activation

Block S120 of the method S100 recites activating surfaces of the substrate 110 and walls of the open network of pores 112. Generally, a chemical or covalent functionalization process is applied to the substrate 110 in order to create defects in surfaces of the substrate 110 to increase an interface area between the substrate 110 and the coating 120.

In one implementation, the heatsink 102 includes a substrate 110 defining a graphite foam and is oxidized via application of an electric potential to the substrate 110 while immersed in a liquid bath. For example, the substrate 110 can be submerged in a dilute acid bath (e.g., a sulfuric acid bath with concentration 1-gram sulfuric acid/1-L distilled water) that acts as an electrolyte solution. The substrate 110 can be electrically coupled to an anode inserted into the liquid bath and segregated from the substrate 110. An electric voltage can then be applied between the substrate 110 and the anode, such as up to an oxidation voltage that yields a target current per-unit surface area of the substrate 110 for a preset oxidation duration, such as: between 100-milliamps and 400-milliamps per-square-centimeter of surface area of the substrate 110 for a period between 10 minutes and 40 minutes. Therefore, surfaces of the substrate 110 can be activated by submerging the substrate 110 in an aqueous bath and exposing the substrate 110 to an electric potential to: oxidize surfaces of the substrate 110; increase surface roughness of surfaces of the substrate 110; and activate surfaces of the substrate 110 to bond with functional hydrophilic groups of the coating 120.

In one variation, multiple substrates are machined into a single graphite foam block, such that multiple substrates can be electrically coupled to the anode and surfaces of the substrates are oxidized via a bridge of graphite foam connecting these substrates. At a later time (e.g., after applying the coating 120), the substrates can be separated (e.g., via a CNC drill).

In another implementation, these surfaces of the substrate 110 are washed with or exposed to surfactants (e.g., sodium dodecyl benzene sulfonate, sodium dodecyl sulfonate) in order to functionalize surfaces of the substrate 110 via a non-covalent functionalization process.

In yet another implementation, these surfaces of the substrate 110 are coated with a polymer including hydrophilic groups (e.g., polydopamine) in order to functionalize surfaces of the substrate 110 via a non-covalent functionalization process.

11. Coating Application

In a first form (e.g., an aqueous cementitious mixture), the coating 120 includes a volume of cement and a volume of water (e.g., distilled water) mixed at an appropriate ratio (e.g., 0.8 water/cement) such that the coating 120 exhibits a viscosity sufficiently low to enable the coating 120 to flow over the surfaces of the substrate 110 and into pores and channels of the open network of pores 112. The coating 120 solution can be mixed separately according to a particular water-cement ratio (e.g., 0.8-g water/1-g cement) for approximately one minute via a mixer (e.g., impellor, vibrator). In one variation, the coating 120 can be mixed at a lower water-cement ratio with the addition of superplasticizers to increase fluidity of the cementitious mixture. Additionally and/or alternatively, the cementitious mixture can include surfactants to lower surface tension and therefore increase fluidity and maneuverability. Furthermore, the coating 120 can be mixed at low temperatures (e.g., five degrees Celsius) such that the cementitious mixture will react or set more slowly. Cement colorants may also be added to the cementitious mixture at concentrations ranging from three-percent to ten-percent of a weight of the cement.

After mixing the coating 120, the coating 120 is deposited on the activated surfaces of the substrate 110 including: the interior surface 114, the exterior surface 116, and the walls of the open network of pores 112. In one variation, the substrate no can be submerged in the coating 120 solution and stirred sufficiently (e.g., for approximately 10-seconds) such that the coating 120 lines the open network of pores 112 of the substrate no and both the exterior and interior surfaces 114 of the substrate 110. Alternatively, the coating 120 may be sprayed onto the substrate no to line the surfaces of the substrate 110 and walls of the open network of pores 112. After the coating 120 is sufficiently applied to the substrate no (e.g., evenly coating each surface of the substrate no and walls of the pores), the substrate no is removed from the cementitious mixture for removal of any excess cementitious mixture and drying.

Therefore, the heatsink 102 can be formed by applying the coating 120 over the substrate 110 including: preparing a mixture of water and cement at a water-cement weight ratio greater than 0.65; agitating the mixture (e.g., via a bubbler, impeller, or vibrator); immersing the substrate no in the mixture; and drying the mixture to form the coating 120 defining a heterogenous microstructure permeable to water over the interior surface 114, the exterior surface 116, and walls of the open network of pores 112.

12. Setting and Pore Cleaning

After the substrate 110 is removed from the cementitious mixture, excess coating 120 can be driven out of the open network of pores within the substrate 110.

In one implementation, after the coating 120 is first applied to the substrate 110 and before the coating 120 dries or hardens, positive pressure is applied to the substrate 110 to force excess coating 120 from the substrate 110. For example, a jet of compressed area can be washed over the substrate 110 and the coating 120 to drive any excess coating through and out of the open network of pores 112. In another example, the interior surface of the substrate 110 is set over and clamped around a bore in a pore-clearing jig, and the bore is pressurized to drive excess coating 120 from the open network of pores in the substrate 110. In this example, the bore can be pressurized with compressed air, nitrogen, or other inert gas (e.g., up to 5 psi): for a preset duration of time (e.g., 5 psi for one minute); until a gas flux (i.e., a volume flow rate) through the pore-clearing jig and substrate 110 exceeds a minimum gas flux corresponding to a maximum obstruction of pores in the substrate 110 by the coating 120; or until a pressure drop across the substrate 110 falls below a maximum pressure drop corresponding to a maximum obstruction of pores in the substrate 110 by the coating 120.

In another implementation, after the coating 120 is first applied to the substrate 110 and before the coating 120 dries or hardens, negative pressure is applied to the substrate 110 to draw excess coating 120 from the substrate 110. For example, the interior surface of the substrate 110 is set over a bore in a pore-clearing jig, and a vacuum is drawn on the bore to suction excess coating 120 from the open network of pores in the substrate 110. In this example, a vacuum can be drawn on the bore: for a preset duration of time (e.g., 250 mmHG for one minute); until a gas flux through the pore-clearing jig and substrate 110 exceeds a minimum gas flux corresponding to a maximum obstruction of pores in the substrate 110 by the coating 120; or until a pressure drop across the substrate 110 falls below a maximum pressure drop corresponding to a maximum obstruction of pores in the substrate 110 by the coating 120.

Furthermore, by applying positive or negative pressure to the substrate 110 while the coating 120 on the substrate 110 is still wet, the coating 120 can be maneuvered throughout the open network of pores 112 in the substrate 110 to contact, coat, and thoroughly line substantially all walls within the open network of pores 112 in the substrate 110. Active removal of excess coating 120 from the substrate 110 can also be controlled (e.g., by time, gas flux through the substrate 110, and/or pressure change across the substrate no) in order to achieve a coating on walls of the internal network of pores in the substrate 110 that yields: a consistent cross-sectional area of pores through the substrate; pores through the substrate that are wide enough to pass water (e.g., human sweat, such as via capillary action); and pores through the substrate that are narrow enough to mechanically obstruct oils.

Therefore, after cleaning the open network of pores in the substrate 110 with positive or negative pressure, a fine and approximately uniform layer of the coating 120 may remain on walls of the internal network of pores in the substrate 110.

The coating 120 and the substrate 110 can then set—such as at room temperature for preset setting duration (e.g., 24-hours)—such that the coating 120 sets (e.g., hardens and solidifies) over the substrate 110 to form the heatsink 102.

13. Base Layer

In one variation, an additional layer of the coating 120 is applied to the interior surface 114 of the substrate 110 such that to form a thicker base layer configured to contact skin of a user and to buffer the substrate 110 from impact against the user's body during use. More specifically, because the porous material of the substrate 110 may be more brittle and exhibit a lower modulus of elasticity than the coating 120, an additional layer of the coating 120 can be applied over the interior surface 114 of the substrate 110 in order to form a more robust interface between the substrate 110 and a user's skin.

For example, an additional layer of the coating 120 can be sprayed onto the interior surface 114 of the substrate 110 to form a thicker base layer that is two millimeters thick and that extends internally through the open network of pores 112 from the edge of the coated substrate 110 by two-millimeters, thereby increasing heat absorption from the user into the heatsink 102, and increasing mechanical robustness of the heatsink 102.

In one variation, a base layer of the coating 120 is applied over the internal surface 114 of the substrate 110 after removing an excess of the coating 120 from the substrate 110 to fill the open network of pores 112 at the base of the substrate 110. For example, an excess of the coating 120 can be removed from the substrate 110 to render the coating 120 of thickness less than 200 microns on walls of the open network of pores 112 in the substrate 110. After the excess coating 120 is removed, a base layer of the coating of thickness greater than one millimeter can be deposited on the interior surface 114 of the substrate 110 and penetrate the open network of pores 112 at a depth of one-millimeter, thereby increasing moisture wicking through the microstructure of the base layer of the coating 120 and increasing contaminant resistance at the interior surface of the substrate 110.

14. Hydration

In one variation, after the coating 120 sets (e.g., solidifies) over the substrate 110, the coated substrate 110 (hereinafter the "heatsink 102") is submerged in a water bath (e.g., distilled water bath) to hydrate the coating 120. While the heatsink 102 is submerged in the water bath, the heatsink 102 is heated from an initial temperature (e.g., ambient temperature) to a cure target temperature (e.g., greater than 60° Celsius) and held at this cure target over a cure duration (e.g., 72 hours; ten days; twenty days).

For example, the heatsink 102 can be submerged in a heated water bath, the heatsink 102 at a first temperature of 20° Celsius. The heatsink 102 can then be gradually heated to a second temperature of 70° Celsius over a duration of five days in order to minimize weakening or fractures of the coating 120 during this period. The heatsink 102 can remain in this heated water bath—held at the second temperature—for an additional five days to complete the hydration process. At this conclusion of this ten-day hydration process, the heatsink 102 can be removed from the water bath, cooled, rinsed with distilled water to remove residue of the hydration process, and dried (e.g., by air-drying at room temperature).

In another variation, the heatsink 102 is exposed to a high-humidity, high-temperature environment during the hydration process. For example, the heatsink 102 can be loaded into a humidity chamber, and the humidity chamber can then drive its internal environment to 70° Celsius while maintaining its internal humidity at a water vapor saturation pressure (i.e., 100% humidity) over a ramp period (e.g., one day). The humidity chamber can maintain its internal environment under this condition for an additional soak period (e.g., two days) before returning its internal environment to ambient conditions during a cool-down period (e.g., four hours), at which time the hydration process is completed and the heatsink is removed from the humidity chamber.

Therefore, after excess coating 120 is removed from the substrate no: the resulting heatsink 102 can be immersed in an aqueous bath during a curing period greater than twenty-four hours; the aqueous bath can be heated to a curing temperature over a first duration of the curing period (e.g., approximately one-third of the duration of the curing period); and the aqueous bath can be held at the curing temperature over a second duration of the curing period in order to hydrate and cure the coating 120. Following conclusion of the curing period, the heatsink 102 can be rinsed and dried.

However, the coating 120 can be hydrated and cured according to any other schedule or schema.

15. Carbonation & Cleaning

During the hydration process, calcium ions present in the coating 120 react with carbon dioxide in the environment to produce calcium carbonate on surfaces of the coating 120. This calcium carbonate may increase mechanical resilience of the coating 120 and therefore increase mechanical resilience of the heatsink 102 as a whole.

However, this calcium carbonate may also decrease porosity of the coating 120 (e.g., by obstructing a void network 121 of the coating 120) and the heatsink 110 more generally (e.g., by obstructing the void network 121 of the coating 120). Therefore, the heatsink 102 can be exposed to a decarbonation process to remove excess calcium carbonate from the coating 120, thereby increasing porosity of the heatsink 102 while maintaining mechanical resilience of the coating 120.

For example, formation of calcium carbonate on the coating 120 applied over surfaces of the substrate 110 and within the open network of pores 112 may increase the mechanical resilience but reduce a porosity of the heatsink 102. To mitigate this reduction in porosity of the heatsink 102, the heatsink 102 can be cleaned with an acid (e.g., hydrochloric acid, acetic acid) to remove excess calcium carbonate from the surface of the cured coating 120—both on the external surfaces of the heatsink 102 and in pores within the open network of pores 112 in the heatsink 102.

Furthermore, to increase permeability of the coating 120 itself to water, and thus increase water-carrying capacity of the heatsink 102, the heatsink 102 can be processed to increase carbonation in the coating 120 and then processed to remove both superficial calcium carbonate on surfaces of the coating 120 and to remove calcium carbonate from the microstructure of the coating 120, thereby introducing a greater concentration of pores that are permeable to water within the coating 120 and increasing exposure of hydrophilic surfaces of the coating 120.

In one example, following completion of the hydration process described above (e.g., after removing the heatsink 102 from the water bath), the heatsink 102 is located in an atmospheric chamber, which is then filled with a high concentration of carbon dioxide (e.g., 10%, 50%, or 100% carbon dioxide) in order to increase a rate of carbonation (i.e., formation of calcium carbonate) within the coating 120 as the coating 120 continues to cure. After soaking in the carbon dioxide-rich environment, the heatsink 102 is then removed from the atmospheric chamber and immersed in an acid bath—such as with a high concentration of hydrochloric acid or acetic acid (e.g., vinegar)—for a short duration (e.g., less than fifteen seconds) to dissolve (or "etch") calcium carbonate from both surfaces of the coating 120 and from the microstructure of the coating 120. Therefore, the heatsink can be: located in a gas environment of a proportion of carbon dioxide greater than 10% to promote formation of calcium carbonate in the coating 120; and rinsed with an acid to remove excess calcium carbonate from the coating 120 along walls of the open network of pores 112 in the substrate no.

Furthermore, carbonation may lower a pH of the coating 120. For example, the coating 120 may exhibit a first pH level (e.g., greater than "9") following the hydration process; such high pH of a surface in contact with human skin may result in irritation or chemical burns over a long exposure. Therefore, the heatsink 102 can be carbonated to reduce the pH of the coating 120 to a second pH level—less than the first pH level (e.g., to between "7" and "8")—such that heatsink may remain in contact with a user's skin over extended periods of time without irritation to the user.

16. Increased Hydrophilicity & Resistance

In one variation, the heatsink 102 includes a second layer applied over the coating 120 and can be configured to increase hydrophilicity and increase contaminant resistance of the heatsink 102 (or the coating 120 more specifically).

In one implementation, a second layer of a methyltrimethoxysilane (or "MTMS") is applied to the heatsink 102 after carbonation of the coating 120 described above. Generally, MTMS may exhibit relatively high compatibility with aqueous processing environments while exhibiting lower environmental impact than fluorinated materials. Additionally, hydroxyl groups of the MTMS layer can bind the coating material (e.g., cement or other desiccants) via hydrogen bonds resulting in condensation and formation of permanent siloxane bonds between the coating 120 and the second MTMS layer. Thus, when applied over the coating 120, the second layer of MTMS may increase water uptake (e.g., from a user's skin) at the contact surface 126 and increase water flow rate through the heatsink 102. For example, MTMS (e.g., deposition grade, 98%) can be mixed with 0.1 molar solution of hydrochloric acid at a 4:1 ratio by volume. This solution can be sonicated in an ice bath for approximately five minutes to induce hydrolysis of the solution. Following the hydration process and/or following the carbonation process described above, the heatsink 102 can be immersed in this hydrolyzed MTMS solution for a coating duration (e.g., two minutes) in order to coat surfaces of the coating 120 with the second layer of MTMS. The heatsink 102 can then be removed from the hydrolyzed MTMS solution, rinsed (e.g., in water), and dried. For example, the heatsink 102 can be blown dry with compressed gas such as described above and then set to dry and cure on a drying rack (e.g., at ambient conditions) for a drying period (e.g., six hours, twelve hours).

Furthermore, prior to immersing the heatsink 102 in the hydrolyzed MTMS solution, the heatsink 102 can be cleaned (e.g., with a solvent) to remove oils and other organic compounds from the heatsink 102. For example, the heatsink 102 can be rinsed with acetone, methanol, and/or isopropanol. The heatsink can then be exposed to an air plasma for approximately five minutes in order to remove solvent residue from the heatsink 102 and to increase presence of hydroxyl groups on surfaces of the coating 120 to application of the second layer of MTMS.

In other implementations, the contact surface 126 of the heatsink 102 is coated with a second layer of silver nitrate, silver nitrite, or other skin-safe metal—such as via electroplating, chemical vapor deposition coating, or sputtering, etc.—in order to form a buffer between a user's skin and the coating 120 and thus reduce possibility of irritation of the user's skin by the coating 120 during use. However, a second layer of any other material can be applied to the coating 120 in any other way in order to increase water uptake and/or reduce skin irritation by the heatsink 102.

17. Silica Gel & Desiccant Structure

In one variation, the hydrophilic coating 120 forms a silica gel structure. In particular, the substrate no defines an open network of pores 112 exhibiting relatively larger sizes and extending throughout a heatsink 102; and the coating 120 defines a porous, hydrophilic microstructure with pores exhibiting relatively smaller sizes and lines interior and exterior surfaces of the substrate to produce—after chemical treatment as described above—a robust, hydrated silica gel structure. To form this hydrated silica gel structure, the coating 120 can include a cement-water mixture or other desiccant-water mixtures.

In this variation, the silica gel coating 120 defines a hydrophilic microstructure with pores exhibiting relatively smaller sizes including micropores of a first size and nanopores (e.g., voids) of a second size smaller than the first size. The silica gel coating 120 can be hydrated such that the nanopores of the coating 120: are hydrated (e.g., filled with water) at normal conditions (e.g., 20° C. at 101.325 kPa); are sufficiently small such that larger hydrophobic molecules cannot displace water in the nanopores; increase hydrophilicity of the coating 120 and thereby the heatsink 102. Further, the silica gel coating can be configured such that micropores of the coating 120 are larger than the nanopores of the coating 120 but smaller than pores of the network of pores 112 such that water freely flows these micropores.

Therefore, the silica gel structure of the coating 120 interacts with the open network of pores 112 of the substrate 110: to wick water from skin of a user through the void network 121 of the coating 120; to prevent oils from displacing water molecules in the void network 121; and to enable air and oils to flow through the larger pores of the network of pores 112.

Alternatively, the hydrophilic coating 120 can include: an alumina; a zeotype; an aluminophosphate; a metal organic framework; a zinc hydrogel; or other desiccants. Because desiccants adsorb water under standard conditions (e.g., 20° C. at 101.325 kPa), the coating 120 may be hydrated with water and therefore exhibit greater, hydrophilicity under such conditions. A hydrophilic coating 120 including a desiccant material can define a hydrophilic microstructure with pores exhibiting relatively smaller sizes including micropores of a first size and nanopores (e.g., voids) of a second size smaller than the first size, similar to the silica gel structure.

Therefore, because the coating 120 includes a silica gel or desiccant material that forms a microstructure of voids of relatively small size (e.g., smaller than pores in the open network of pores 112 of the substrate no), the coating 120 restricts displacement (or "replacement") of water molecules in voids of the coating 120 by contaminant molecules (e.g., oils). For example, the coating can include a desiccant forming a void network 121 defining a microstructure of nanopores exhibiting widths (or diameters) less than 1.0 nanometer such that water molecules may fill these voids (or "pores") and such that these voids reject uptake of larger hydrophobic molecules, such as oils from a user's skin.

18. Wearable Heatsink

In one variation, the heatsink 102 is integrated into or connected to a textile to form a wearable heatsink configured to attach to a user or to be worn by a user and to retain the contact surface 126 of the heatsink 102 in contact with the user's skin.

In one implementation, the dermal heatsink 100 includes a textile panel 130 defining a first aperture 132; and the heatsink 102 is arranged in the first aperture 132 with an interior surface 114 of the substrate 110 approximately coplanar with the textile panel 130. In this implementation, the dermal heatsink 100 further includes a heatsink retainer 140 bonded to the textile panel 130 about a periphery of the first aperture 132 and bonded to a perimeter of the heatsink 102 and/or mechanically retaining the heatsink 102 to the textile panel 130.

18.1 Heatsink Retainer: Polymer Frame

In one implementation, the heatsink 102 attaches to the textile panel 130 via a polymer frame encircling the thermally conductive heatsink. In one variation, the heatsink retainer 140 is a square shaped, thermoplastic polymer. Alternatively, the heatsink retainer 140 can be machined from aluminum or cement. The heatsink retainer 140 can securely attach the heatsink 102 to the textile panel 130 and increase the mechanical resilience of the heatsink 102. The heatsink retainer 140 can be adhered to the textile panel 130 by partially melting or injecting the frame into the textile panel 130 and the heatsink 102. In one variation, a first heatsink retainer 140 is attached to a perimeter of an aperture of the textile panel 130 before inserting the heatsink 102 into the aperture. Upon insertion of the heatsink 102, a second heatsink retainer 140 is melted into the perimeter of the heatsink 102 and the perimeter of the aperture to secure the heatsink 102. Additionally, the heatsink retainer 140 can include a set of claws 142 configured to extend between fins of the heatsink 102 for additional security.

18.2 Multiple Heatsinks

In one implementation, the heatsink 102 can be integrated into a dermal heatsink 100 including multiple heatsinks 102 and defining a headband 160 configured to be worn by a user such that the heatsink 102 contacts skin on a forehead of the user. In this example, the dermal heatsink 100 can include: a textile panel 130 defining a first aperture 132; a heatsink 102 defining a substrate 110 and a coating, the heatsink 102 arranged in the first aperture 132 with an interior surface 114 of the substrate 110 approximately coplanar with the textile panel 130; and a heatsink retainer 140 bonded to a perimeter of the heatsink 102 and bonded to the textile panel 130 about a periphery of the first aperture 132.

In this implementation, the dermal heatsink 100 can include: a second heatsink arranged in a second aperture 133 defined by the textile panel 130, the second heatsink defining a second substrate and a second coating. The second substrate defines: a second interior surface 114 configured to thermally couple to a second heat source 150; a second exterior surface 116; and a second open network of pores extending between the second interior surface 114 and the second exterior surface 116. The second coating includes the hydrophilic, contaminant resistant material: extending across the second exterior surface 116 of the second substrate; extending across the second interior surface 114 of the second substrate; and lining the second open network of pores within the second substrate.

The second heatsink can include a second polymer frame bonded to a second perimeter of the second heatsink and bonded to the textile panel 130 about a second periphery of the second aperture 133. In this example, each heatsink and therefore each aperture can be approximately two-inches in length.

A gap between the two heatsinks 102 on the textile panel 130 enables the textile panel 130 to bend according to the shape of a user's forehead.

To prevent collisions between adjacent heatsinks 102 on the textile panel 130, polymer frames about adjacent heatsinks 102 are configured to collide between each other before the heatsinks 102 can collide. For example, the plastic frames can be configured to exhibit a certain height such that a first angle of collision of the polymer frames is less than a second angle of collision of the heatsinks 102.

18.3 Heatsink Pattern

In one implementation, the dermal heatsink 100 is configured to fit according to a curvature of a human body. For example, the dermal heatsink 100 can include: a textile vest configured to be worn on a human torso and defining a grid array of apertures; and a set of heatsinks 102, each heatsink in the set of heatsinks 102 retained in an aperture in the set of apertures in the textile panel 130. The set of heatsinks 102 can be configured to: contact skin on a torso of a user when the textile vest is worn by the user; and wick moisture from skin of the torso of the user to cool the user. The grid array of apertures can be arranged in a pattern such that when the textile vest is worn by the user, it is flexible about the curvature of the torso of the user. In one variation, the grid array of apertures are arranged according to a Voronoi geometry, such that the dermal heatsink 100 can cover complex 3D surfaces (e.g., of the human body) and dissipate heat from the heat source 150 (e.g., a human body) efficiently. For example, the dermal heatsink 100 can include: a textile vest configured to be worn on a human torso and defining a grid array of apertures; and a set of heatsinks 102 comprising the heatsink 102, each heatsink 102 in the set of heatsinks 102 retained in an aperture in the set of apertures in the textile vest and arranged in a Voronoi pattern. The set of heatsinks 102 can be configured to: contact skin on a torso of a user when the textile vest is worn by the user; and wick moisture from skin of the torso of the user to cool the user.

In one variation shown in FIGS. 2A and 2B, the dermal heatsink 100 is configured to include heatsinks 102 of varying shape and size such that the dermal heatsink conforms to different regions of the body exhibiting different curvature. For example, a dermal heatsink 100 can be configured to be worn about a forearm of a user. The dermal heatsink can include: a first heatsink of a first size configured to contact skin on a first region of the forearm corresponding to a dorsal side of the forearm; a second heatsink of a second size configured to contact skin on a second region of the forearm corresponding to a side of the forearm, the second size less than the first size. Therefore, heatsinks 102 configured to contact skin in regions of the body exhibiting greater curvature (e.g., the wrist) can be machined to smaller sizes than heatsinks 102 configured to contact skin in regions of the body exhibiting flatter surfaces (e.g., the abdomen) in order to maximize a surface area of skin covered by heatsinks 102 such that heat is dissipated from skin of the user by the heatsink 102 at a higher rate, thus cooling the user more quickly.

18.4 Removable Heatsinks and Textile Panel

In the foregoing implementations, the heatsink 120 is intransiently bonded or coupled to the textile panel 130 (e.g., by the heatsink retainer 140), which forms a complete article of clothing, such as a shirt, a headband, or an armband. Alternatively, the textile panel 130—with integrated heatsink 102—can be configured to transiently install on a garment and to be removed from the garment, such as when the garment is washed or to replace the textile panel 130 and heatsink 102 with a new unit of the textile panel 130 and integrated heatsink 102 when the former is soiled after repeated use. For example, the textile panel 130—with integrated heatsink 102—can include snaps or buttons configured to attach or engage to corresponding features on a shirt or other garment. In another example, the textile panel 130—with integrated heatsink 102—can be configured to transiently couple to an article of clothing via a hook and loop fastener or a zip fastener.

In another implementation, the heatsink retainer 140 is configured to transiently retain an individual heatsink 102 to the textile panel 130, thereby enabling the individual heatsink 102 to be removed from the textile panel 130 when a garment containing the textile panel is washed or when the heatsink 102 is replaced with a new heatsink 102. For example, the set of claws 132 in the heatsink retainer 140 can be retractable to release the heatsink from the heatsink retainer 140.

However, the heatsink 102 can be transiently or intransiently coupled to the textile panel 130 in any other way, and the textile panel 130 can form directly or can be transiently coupled to a garment in any other way and in any other format.

19. Dermal Heatsink Examples

In the foregoing variation, the textile panel 130 can form or can be integrated into the dermal heatsink 100 configured to be worn by a user and to retain a set of heatsink 102 in contact with the user's skin. For example, the dermal heatsink 100 can define a textile or clothing article including: a cap; a shoe; a helmet; a shirt; a vest; a headband; a wristband; an armband; or protective gear; etc.

19.1 Example: High Sweat Rate Areas

In one variation, the dermal heatsink 100 includes a cluster or group of heatsinks 102 and is configured to locate these heatsinks 102 in a region of a human body associated with a relatively high sweat rate (e.g., where sweating by a human body is commonly most profuse) in order to achieve a consistent, high rate of heat dissipation from a user's body during intensive exercise or activity by the user. For example, in this variation, the dermal heatsink 100 can be configured to locate a cluster of heatsinks 102 on a region of the human body typically containing a relatively high density of sweat glands and/or containing a relatively high density of superficial veins proximal the surface of the skin.

For example, a dermal heatsink can be configured to be worn across an abdomen of a human user. In this example, the dermal heatsink can include: a first set of heatsinks 102 exhibiting a first total area of contact surfaces 126 configured to contact the user's skin on a dorsal region of the abdomen; and a second set of heatsinks 102 exhibiting a second total area—less than the first total area—of contact surfaces 126 configured to contact skin on a side region flanking the user's abdomen. In this example, because the user's abdomen may produce a higher volume of sweat due to the higher density of sweat glands in this region of the body, the second set of heatsinks 102 located over the user's flank may span a smaller surface area of the user's body than the first set of heatsinks 102 located over the user's abdomen. Therefore, the dermal heatsink 100 may locate more heatsinks 102 in regions of the user's body at which more sweat is produced in order to maintain high thermal extraction efficiency (i.e., "cooling") of the user; and vice versa in order to limit complexity of the dermal heatsink 100.

The dermal heatsink 100 can define a headband configured to be worn across the forehead of a human user. For example, the dermal heatsink 100 can define: a textile panel of rectangular shape of a length less than ten inches and a width less than three inches; a set of heatsinks 102 arranged in a row within the textile panel, such that heatsinks in the set of heatsinks 102 contact skin on a human user's forehead. The textile panel can be incorporated into a headband (via laser cutting or sewing techniques) such that the headband may be worn about a human user's head, and the textile panel including the row of heatsinks 102 contacts skin of the human user's forehead when the headband is worn. In this example, a user's head including the forehead may produce a high volume of sweat due to the higher density of sweat glands in this region of the body, however, a back side of the head may produce less sweat absorbable by the heatsinks 102 due to hair from the head decreasing contact between the heatsinks 102 and skin on the head of the user. Therefore, the dermal heatsink 100 may locate more heatsinks 102 on a portion of the headband in contact with the forehead of the user.

The dermal heatsink 100 can define a vest configured to be worn on a human torso. For example, the vest can include: a textile panel defining a textile vest configured to be worn on a torso of a human user and a set of apertures; a first grid array of heatsinks 102 including a first quantity of heatsinks, each heatsink in the first grid array of heatsinks 102 retained in an aperture in the set of apertures such that each heatsink in the first grid array of heatsinks 102 contacts skin on a chest of a human user wearing the vest; a second grid array of heatsinks 102 including a second quantity of heatsinks 102, the second quantity less than the first quantity of heatsinks 102, each heatsink 102 in the second grid array of heatsinks 102 retained in an aperture in the set of apertures such that each heatsink 102 in the second grid array of heatsinks 102 contacts skin on a lateral torso of a human user wearing the vest. Therefore, in this example, the vest locates a higher quantity of heatsinks 102 at a chest region of the human body than at a lateral region of the human body, as a greater volume of sweat may be produced at the chest region than the lateral region.

The dermal heatsink 100 can define a glove configured to be worn over a human hand. For example, the dermal heatsink 100 can define: a textile panel exhibiting a square shape of side lengths less than three inches such that the textile panel fits approximately within a palm of a human user; a set of four heatsinks 102 arranged in a square pattern within the textile panel, such that each heatsink 102 contacts skin on the palm of the user. The textile panel can be incorporated into a glove (via laser cutting or sewing techniques) such that the glove may be worn over a human user's hand. In this example, the glove locates heatsinks 102 within the glove at the palmar side of the hand rather than at the dorsal side of the hand, due to the higher density of sweat glands in the palmar region than the dorsal region of the hand.

19.2 Example: High-Impact Areas

In one variation, the dermal heatsink 100 is configured to locate a cluster of heatsinks 102 over a region of a human body where possibility of impact in low in order to limit damage to the dermal heatsink 100 during use and thus maintain a high and consistent rate of cooling for a user over time. For example, a first dermal heatsink 100 designated for a runner can be configured to locate a cluster of heatsinks 102 in contact with skin on the runner's forehead; and a second dermal heatsink 100 designated for a soccer player can be configured to locate a cluster of heatsinks 102 in contact with the player's abdomen, which may experience less impact than the player's forehead and chest.

19.3 Example: Medical Garment

In one implementation, the dermal heatsink 100 can be worn or attached to a user for medical purposes. For example, the dermal heatsink 100 can attach or be worn on the forehead (e.g., in a headband 160) of a user exhibiting a fever (e.g., higher than normal body temperature) to rapidly cool the body temperature of a user to a normal temperature (e.g., 98.6° Fahrenheit). The user may wet or drench the heatsink 102 before attaching the dermal heatsink to her body such that heat transfer from her skin to the heatsink 102 occurs immediately upon attaching the dermal heatsink.

In another example, a set of heatsinks 102 are incorporated into a textile panel 130 to define a dermal heatsink 100 in the form of a vest. In this example, a patient exhibiting a high fever may wear the vest to reduce a body temperature of the user. The patient or medical staff may douse the vest with water to increase a rate of cooling. In particular, due to minimal airflow through the vest, the vest can be paired with a fan to further increase the rate of cooling such that the body temperature of the patient decreases at a high rate.

19.4 Example: Athletic Gear

Figure 3B:
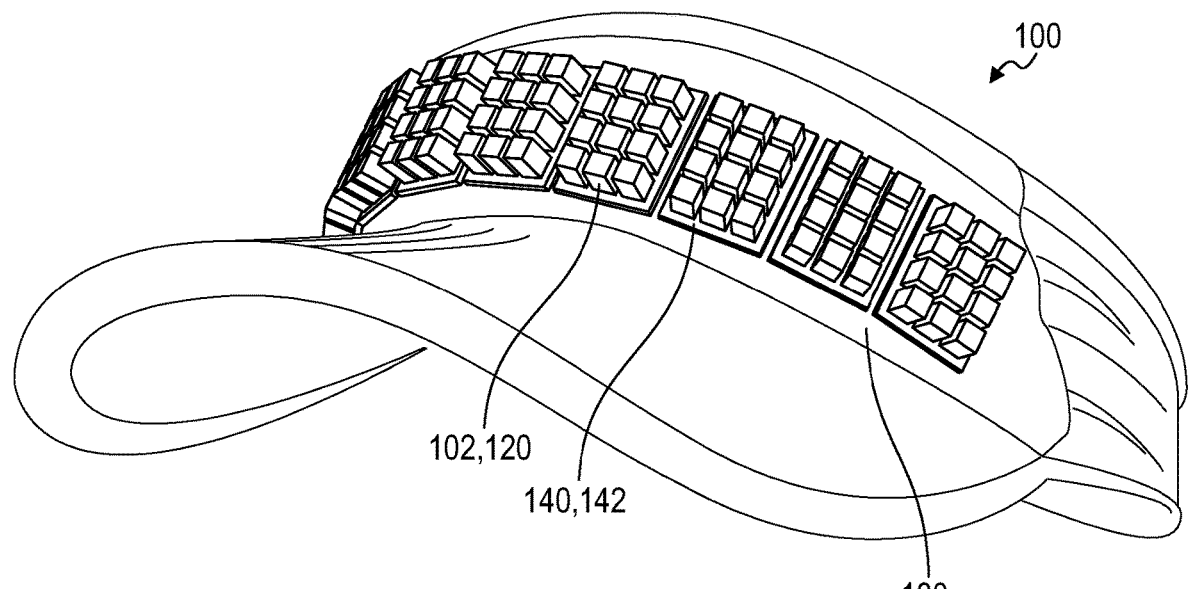
Figure 3C:
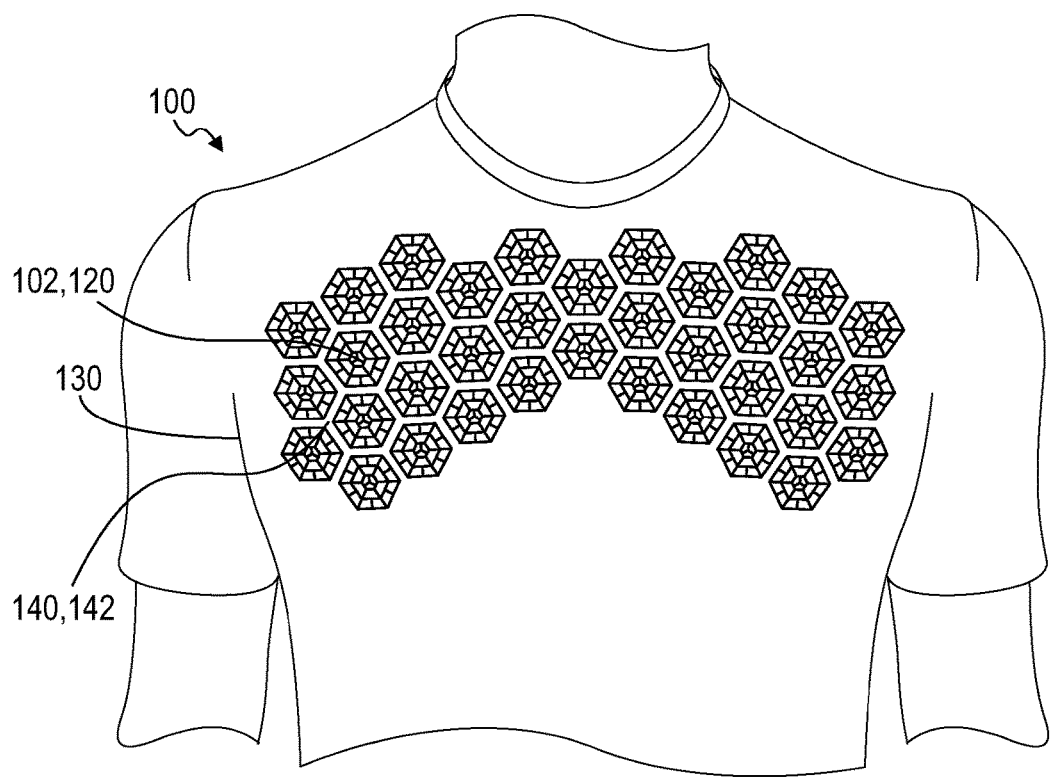
Figure 3D:
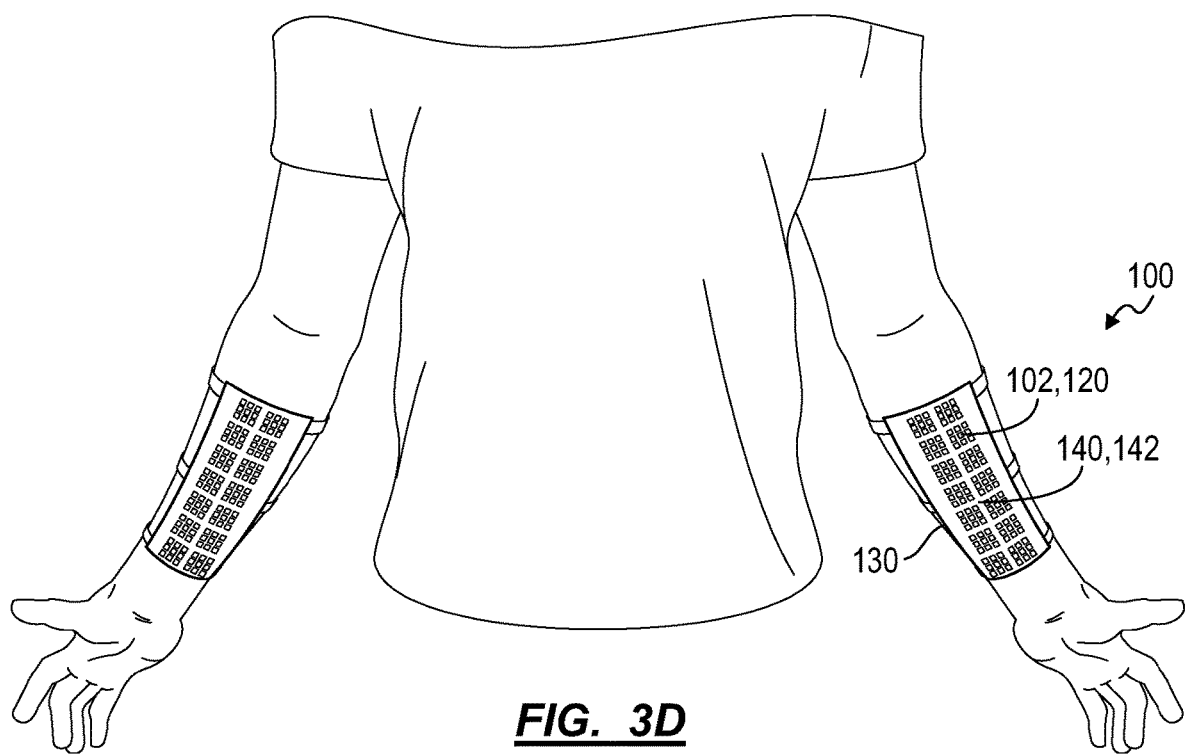

In one variation, the dermal heatsink 100 is incorporated into athletic gear (e.g., sports uniforms). For example, the dermal heatsink 100 can be configured to be worn in the sole of a cleat for baseball players. In another example, as shown in FIG. 3B, the dermal heatsink 100 can define a visor. In this example, the heatsinks 102 can be permanently attached to the visor via the heatsink retainer 140 and the set of claws 132. In yet another example, the dermal heatsink can be configured to be worn on a chest guard or underneath a chest guard of a football player. In this example, shown in FIG. 3C, the dermal heatsink 100 can be configured to contact a chest of the user and exhibit a shape that naturally fits the curvature of the human chest. Therefore, a perimeter of the dermal heatsink configured to be worn on the chest can exhibit a particular shape distinct from an outline of the dermal heatsink configured to be worn on the forehead of the user. Additionally, the shape and size of each individual heatsink 102 may vary according to the curvature of the chest as opposed to that of the forehead. In another example, the dermal heatsink 100 can be configured to be worn on the forearms of a user, as shown in FIG. 3D. In this example, the heatsinks 102 can be configured to contact skin of the user where sweating is most abundant, such as on the ventral side of the forearm which typically produces more sweat than on the dorsal side of the forearm. Additionally, by locating the heatsinks 102 on the ventral side of the forearm, the heatsinks 102 may be less likely to experience contact or impact from an external source, and therefore may depreciate more slowly.

19.5 Example: Daily Apparel

In one variation, the dermal heatsink 100 is incorporated into apparel worn outside of exercise for everyday wearing by a user. For example, the dermal heatsink 100 can be configured to attach to a collar of a shirt, such that the dermal heatsink is not visible on an exterior of the shirt and a user may wear the dermal heatsink to wick sweat around the neck region and to stay cool. In this example, the dermal heatsink 100 can be removable such that it is transferable between different items of clothing via a set of fasteners, such as a hook and loop fastener.

To increase a rate of cooling, the user may drench the dermal heatsink 100 with liquid prior to and/or during use. The heatsink 102 can absorb body heat from the user in order to evaporate this liquid. Therefore, the apparatus can dissipate heat from the user or heat source 150 in the absence of sweat and/or physical activity by the user. In one variation, the dermal heatsink 100 includes a liquid reserve configured to distribute liquid to the heatsink 102 passively or actively by the user. Alternatively, liquid can be applied to the heatsink 102 via capsules of a saturated high absorbent material (e.g., a polyurethane sponge) or via an external source (e.g., a hose).

19.6 Example: Mechanical Equipment

In one variation, the dermal heatsink 100 is incorporated into machinery to cool parts of a machine that may produce heat when in use. The heatsink 102 can be scaled appropriately to cool both small-scale and large-scale machinery including: portable electronics, computers, motors, cooling towers, chillers, heat exchangers, etc.

For example, the heatsink 102 can be configured to attach to a surface of a computer, such that heatsink does not interfere with regular use of the computer. In this example, the heatsink 102 can be removable such that it is transferable between different devices or the heatsink 102 can be rigidly attached to a surface of the computer. The heatsink 102 can absorb heat generated by the computer, thereby regulating the temperature of the computer such that the computer does not overheat.

20. Variation: Direct-to-Body Attachment

In one variation, the textile panel 130 defines a thin layer of flexible silicone that can be directly adhered to human skin via an adhesive. For example, the dermal heatsink 100 can include: a thin layer of flexible silicone defining a set of apertures; an epoxy layer applied to an inner surface of the thin layer of flexible silicone, the inner surface approximately coplanar with the interior surface 112 of the substrate 110. In this example, the dermal heatsink 100 can be adhered directly to human skin by applying the inner surface of the thin layer of flexible silicone to human skin, such that interior surfaces 112 of the heatsinks 102 contact skin of the user. Therefore, the dermal heatsink 100 can be located at different regions of the human body to dissipate heat from the user or heat source 150, and is not limited to a particular region of the human body.

21. Metal Substrate

In one implementation, the substrate 110 is molded from a metallic material, such as aluminum or copper. In this implementation, the substrate 110 can be molded to fit a particular size and geometry. The network of pores 112 can be machined or carved into this metallic substrate.

In this implementation, the substrate 110 is cleaned with a set of solvents and layer of oxide is formed on surfaces of the substrate 110. To further functionalize surfaces of the substrate 110 before applying the coating 120, a mixture of hydrochloric acid and sodium hydroxide can be used to etch the surfaces of a metal substrate via submersion of the substrate 110 in an acid bath. For example, a metal substrate (e.g., aluminum substrate) can be submerged in an aqueous solution of 5-wt % sodium hydroxide for approximately 120-seconds. The substrate 110 is then removed from the sodium hydroxide solution and submerged in a 3-wt % hydrochloric acid for approximately 300-seconds at 40° Celsius. Finally, the substrate 110 can be removed from the hydrochloric acid solution and submerged again in the sodium hydroxide solution for 300-seconds. In one variation, for a copper substrate, the substrate 110 can be further oxidized by submerging the substrate 110 in a nitric acid bath to achieve further oxidation.

As a person skilled in the art will recognize from the previous detailed description and from the figures and claims, modifications and changes can be made to the embodiments of the invention without departing from the scope of this invention as defined in the following claims.

We claim:
1. An apparatus comprising:
   a heatsink comprising:
      a substrate comprising a thermally conductive material and defining:
         an interior surface configured to thermally couple to a heat source;
         an exterior surface; and
         a network of pores extending between the interior surface and the exterior surface; and
      a coating:
         comprising a porous, hydrophilic material;
         extending across surfaces of the substrate; and
         lining the network of pores;
         configured to cooperate with the substrate to wick moisture from a surface of the heat source, through the network of pores, to the exterior surface;
   a textile panel defining an aperture configured to receive the heatsink with the interior surface of the substrate approximately coplanar the textile panel; and
   a heatsink retainer coupled to a perimeter of the heatsink and configured to mate with the textile panel to retain the heatsink within the aperture.

2. The apparatus of claim 1, wherein the heatsink retainer is bonded to the textile panel about a periphery of the aperture.

3. The apparatus of claim 1:
wherein the heat source comprises a human body wearing the textile panel;
wherein the surface of the heat source comprises skin of the human body; and
wherein the substrate and the coating cooperate to wick moisture from skin of the human body, through the network of pores, and to the exterior surface.

4. The apparatus of claim 1:
wherein the textile panel comprises a headband configured to be worn about a forehead of a human body; and
wherein the coating is configured to cooperate with the substrate to wick moisture from the forehead of the human body wearing the headband, through the network of pores, and to the exterior surface, to cool the human body.

5. The apparatus of claim 1, wherein the textile panel comprises a vest:
configured to be worn about a torso of a human body; and
defining a grid array of apertures comprising the first aperture and configured to receive a set of heatsinks comprising the heatsink, each heatsink, in the set of heatsinks, configured to:
contact skin of the torso of the human body wearing the vest; and
wick moisture from skin of the torso to cool the human body.

6. The apparatus of claim 1, wherein the substrate comprises:
a base defining the interior surface; and
a set of fins extending from the base, opposite the interior surface, and defining the exterior surface.

7. The apparatus of claim 1:
further comprising a second heatsink comprising:
a second substrate comprising the thermally-conductive material and defining:
a second interior surface configured to thermally couple to the heat source;
a second exterior surface; and
a second network of pores extending between the second interior surface and the second exterior surface; and
a second coating:
comprising the porous, hydrophilic material;
extending across surfaces of the second substrate;
lining the second network of pores; and
configured to cooperate with the second substrate to wick moisture from the surface of the heat source, through the second network of pores, to the second exterior surface;
wherein the textile panel defines a second aperture, offset the first aperture, configured to receive the second heatsink with the second interior surface of the second substrate approximately coplanar the textile panel; and
further comprising a second heatsink retainer bonded to a second perimeter of the second heatsink and configured to the mate with the textile panel to retain the second heatsink within the second aperture.

8. The apparatus of claim 1, wherein the coating comprises:
a dermal shell extending across the interior surface of the substrate and defining a contact surface configured to contact the surface of the heat source, the contact surface defining a first area;
an interior shell lining the open network of pores between the interior surface and the exterior surface; and
an exterior shell:
extending across the exterior surface of the substrate; and
cooperating with the interior shell to define an evaporative surface of a second area greater than the first area.

9. The apparatus of claim 1:
wherein the substrate defines the network of pores comprising pores of a pore size approximately between 0.8 millimeters and 1.6 millimeters; and
wherein the coating defines a thickness between 50 microns and 200 microns.

10. The apparatus of claim 1, wherein the coating exhibits a thickness less than 125 microns.

11. The apparatus of claim 1:
wherein the coating defines a void network of voids exhibiting widths less than 1.0 nanometer.

12. The apparatus of claim 1, wherein, during application to the substrate and before drying, the coating:
comprises a first volume of water mixed with a second volume of cement; and
defines a ratio of the first volume of water to the second volume of cement greater than 0.65.

13. The apparatus of claim 1:
wherein the substrate comprises a graphite foam exhibiting a first impact resistance; and
wherein the coating comprises a cementitious matrix exhibiting a second impact resistance greater than the first impact resistance.

14. An apparatus comprising:
a textile panel defining an aperture; and
a heatsink configured to permanently or removably install within the aperture and comprising:
a substrate comprising a thermally conductive material and defining:
an interior surface configured to thermally couple to a heat source;
an exterior surface; and
an open network of pores extending between the interior surface the exterior surface; and
a coating:
comprising a porous, hydrophilic material;
defining a void network:
comprising voids exhibiting widths less than 1.0 nanometer; and
configured to filter hydrophobic molecules;
extending across surfaces of the substrate;
lining the open network of pores; and
cooperating with the substrate to wick moisture from a surface of the heat source, through the void network lining the open network of pores, to the exterior surface.

15. The apparatus of claim 14:
wherein the heatsink is configured to transiently install within the aperture with the interior surface of the substrate approximately coplanar with the textile panel; and
wherein the textile panel is configured to attach to an article of clothing worn by a user.

16. An apparatus comprising:
a heatsink comprising:
a substrate:
exhibiting a first durability;
comprising a thermally conductive graphite foam; and defining:
an interior surface configured to thermally couple to a heat source;
an exterior surface; and
an open network of pores extending between the interior surface and the exterior surface; and
a coating:
comprising a porous, hydrophilic material comprising a cementitious matrix;
extending across the exterior surface of the substrate;
extending across the interior surface of the substrate;
lining the open network of pores within the substrate;
cooperating with the substrate to exhibit a target durability; and
cooperating with the substrate to:
exhibit the target durability greater than the first durability; and
wick moisture from a surface of the heat source, through the open network of pores, to the exterior surface.

17. The apparatus of claim 16:
wherein the thermally-conductive graphite foam exhibits a first impact resistance; and
wherein the coating exhibits a second impact resistance greater than the first impact resistance.

18. The apparatus of claim 16:
further comprising a textile panel defining an aperture configured to receive the heatsink;
and
wherein the textile panel is configured to attach to an article of clothing worn by a user.

* * * * *